US010458779B2

United States Patent
Haitjema et al.

(10) Patent No.: US 10,458,779 B2
(45) Date of Patent: Oct. 29, 2019

(54) METHOD AND APPARATUS FOR INNER DIAMETER MEASUREMENT OF TRANSPARENT TUBE

(71) Applicant: MITUTOYO CORPORATION, Kanagawa (JP)

(72) Inventors: Han Haitjema, Eindhoven (NL); Hendrik Ketelaars, Gemert (NL)

(73) Assignee: MITUTOYO CORPORATION, Kanagawa (JP)

( * ) Notice: Subject to any disclaimer, the term of this patent is extended or adjusted under 35 U.S.C. 154(b) by 0 days.

(21) Appl. No.: 16/054,340

(22) Filed: Aug. 3, 2018

(65) Prior Publication Data
US 2019/0271535 A1 Sep. 5, 2019

(30) Foreign Application Priority Data

Mar. 1, 2018 (EP) .................................... 18159537

(51) Int. Cl.
*G01J 1/42* (2006.01)
*G01B 11/12* (2006.01)
*G01B 11/255* (2006.01)

(52) U.S. Cl.
CPC ............ *G01B 11/12* (2013.01); *G01B 11/255* (2013.01); *G01J 1/4257* (2013.01)

(58) Field of Classification Search
CPC ....... G01B 11/12; G01B 11/255; G01J 1/4257
(Continued)

(56) References Cited

U.S. PATENT DOCUMENTS 4,441,811 A * 4/1984 Melezoglu ........... G01N 21/412
356/128
4,692,629 A 9/1987 Nakamura
(Continued)

FOREIGN PATENT DOCUMENTS

JP S57-72003 A 5/1982
JP 2000-266518 A 9/2000
JP 2011-106817 A 6/2011

OTHER PUBLICATIONS

Jablonski et al., "Laser Measurement of Form and Dimensions of Transparent Tubular Elements", Measurement, Institute of Measurement and Control. London, GB, vol. 13, No. 1, Mar. 1, 1994, pp. 13-22.
(Continued)

*Primary Examiner* — Isiaka O Akanbi
(74) *Attorney, Agent, or Firm* — Greenblum & Bernstein, P.L.C.

(57) ABSTRACT

In a method and apparatus for measuring a property of a transparent tubular object, a laser beam scans the object, and laser light originating from the object is detected in a first detection direction parallel to the laser beam direction, or in the first and in a second detection direction at an angle thereto, in particular at 90°. The inner radius of the object may be calculated from the refractive index, scanning speed, outer diameter detected in the first detection direction, and, in the second detection direction, the time difference between laser light reflected from the outer surface of the object and laser light refracted into the object and reflected at the inner surface thereof. If the time of detecting laser light refracted into the object and reflected at the inner surface thereof in the first detection direction is known, the refractive index is not required.

16 Claims, 13 Drawing Sheets

(58) Field of Classification Search
USPC .......................... 356/601–624, 632, 660, 517
See application file for complete search history.

(56) References Cited

U.S. PATENT DOCUMENTS

| | | | | |
|---|---|---|---|---|
| 4,859,861 | A * | 8/1989 | Mersch | G01B 11/08 250/559.22 |
| 5,118,954 | A * | 6/1992 | Grosso | G01B 11/105 250/559.24 |
| 7,835,013 | B2 * | 11/2010 | Jones | G01N 21/45 356/517 |
| 9,103,651 | B2 | 8/2015 | Haitjema et al. | |
| 9,568,304 | B2 | 2/2017 | Haitjema et al. | |
| 10,060,727 | B2 | 8/2018 | Imaizumi | |
| 2008/0198389 | A1 * | 8/2008 | Yoo | G01B 11/105 356/626 |
| 2010/0259769 | A1 * | 10/2010 | Kataoka | G01B 11/2433 356/625 |
| 2012/0170036 | A1 * | 7/2012 | Johansen | G01N 21/553 356/369 |
| 2014/0340694 | A1 * | 11/2014 | Fukuda | G01B 11/08 356/635 |
| 2014/0362383 | A1 | 12/2014 | Haitjema et al. | |
| 2015/0276390 | A1 * | 10/2015 | Imaizumi | G01B 11/08 356/601 |
| 2017/0167852 | A1 * | 6/2017 | Miki | G01B 11/08 |
| 2017/0167854 | A1 | 6/2017 | Imaizumi | |
| 2017/0307546 | A1 * | 10/2017 | Fukuda | G01M 11/0278 |
| 2018/0031415 | A1 | 2/2018 | Haitjema et al. | |

OTHER PUBLICATIONS

Search Report issued in EP Patent Application No. 18159537.2, dated May 17, 2018.

* cited by examiner

METHOD AND APPARATUS FOR INNER DIAMETER MEASUREMENT OF TRANSPARENT TUBE

CROSS-REFERENCE TO RELATED APPLICATIONS

The present application claims priority under 35 U.S.C. § 119 of European Application No. 18159537.2, filed on Mar. 1, 2018, the disclosure of which is expressly incorporated by reference herein in its entirety.

BACKGROUND OF THE INVENTION

1. Field of the Invention

The disclosure relates to the field of measuring dimensions of transparent tubular objects, and more specifically to the field of measuring an inner diameter of a transparent tubular object. In particular, the disclosure relates to a method and apparatus for measuring an inner diameter of a transparent tubular object, using laser scanning. Herein, a diameter is taken as twice a radius, so that when an inner radius is measured, thereby an inner diameter being twice the inner radius has been measured.

Herein, a tubular object is understood as an object having a tubular shape, in particular a cylindrical shape, at least at the portion thereof of which the dimensions are measured.

2. Description of Related Art

Various apparatus and methods for measuring diameters of elongate cylindrical or tubular objects are known, as exemplified in the following.

U.S. Pat. No. 4,692,629 A discloses, as part of the related art discussed in this reference, an optical type measuring device wherein a rotary scanning light beam (a laser beam) generated by a polygonal rotary mirror is converted by a collimator lens into a parallel scanning light beam to be passed through this collimator lens and a condensing lens. A workpiece to be measured is interposed between the collimator lens and the condensing lens, and dimensions of the workpiece to be measured are measured from the time length of a dark portion or a bright portion generated due to the obstruction of the parallel scanning light beam by the workpiece to be measured. A similar device is disclosed in JP 2011-106817 A.

The optical type measuring device according to the related art in reference U.S. Pat. No. 4,692,629 or according to reference JP 2011-106817 A is used to measure an outer diameter of a cylindrical workpiece, and no indication whatsoever is given for measuring an inner diameter of a tubular transparent workpiece.

US 2017/0167854 A1 discloses placing a transparent tube in a parallel laser light beam emitted from a light projector and reaching a photoreceiver. The photoreceiver provides a detection signal indicating an amount of light received corresponding to a width direction position of the parallel laser light beam. Peaks formed in the detection signal by beams reflected by an inner circumferential surface of the transparent tube and incident to the photoreceiver are detected; width direction positions of two intersection points where the peaks cross a predetermined threshold value are detected. The width direction positions of the light beam reflected by the inner circumferential surface of the transparent tube are calculated from an average value of the two intersection points. An internal diameter of the transparent tube is measured from the width direction positions.

The method according to reference US 2017/0167854 A1 allows to measure an inner diameter as well as an outer diameter of a transparent tube, by virtue of a laser beam being transmitted tangential to, and through the tube at right angles to its longitudinal extension. Although the reference provides an improvement in a determination of the inner diameter of a transparent tube, there is still room for further improvement of the accuracy of the measurement of the inner diameter, in particular when the transparent tube is thin. Disadvantageously, the method described in US 2017/0167854 A1 becomes insensitive for thin tubular objects as the refraction at the inner surface of the tubular object makes the time difference between the reflections of the laser beam at the inner and outer surface of the tubular object very small.

In Jablonski, R. et al., "Laser measurement of form and dimensions of transparent tubular elements", Measurement 13, 1994, 13-22, a non-contact laser scanning-reflection method is disclosed which enables to measure the total geometry of transparent tubular objects. A focused laser beam is scanned at a constant velocity perpendicular to the object. Three dominant rays are obtained: a first and a second ray represent two reflected waves from the outer and inner surface, respectively, and a third ray represents a wave tangent to the outer surface. The rays are collected by detector lenses of two detectors and converged to a focus in the planes of corresponding detectors. By measuring times between the dominant rays and assuming constant scanning velocity, the outer and inner radii of curvature of the measured object can be determined.

The method according to the Jablonski et al. reference allows the inner diameter of a transparent tubular object to be measured locally at a specific position along the inner circumference of the object. The outer diameter is determined from the reflection at a specific position along the outer circumference of the object. So, this measurement is sensitive to the local curvature. The limited accuracy of the outer diameter measurement adversely affects the inner diameter accuracy.

Accordingly, there is a need to improve the accuracy of a measurement of the inner diameter of a transparent tubular object, in particular in cases where the tubular object is thin, i.e. in cases where the wall thickness of the tubular object is less than about 10% of the radius of the tubular object.

SUMMARY OF THE INVENTION

It is desirable to provide a method and apparatus providing an improved accuracy of measuring an inner diameter of a transparent tubular object.

To better address this concern, in a first aspect of the disclosure a first, second, third, and fourth include of a method for measuring an inner diameter of a transparent tubular object are provided. The tubular object is made from a material having a refractive index, n. The tubular object, at least at the region where the measurement is made, forms a cylinder-shaped channel and has a central axis extending centrally in the channel. The first include of the method includes:

scanning a laser beam in a scanning direction with a constant scanning speed, $v_s$, along a scanning path at right angles to the longitudinal axis of the object, wherein the scanning laser beam is directed in a first laser beam direction to the object at right angles to the scanning direction and at right angles to the longitudinal axis of the object;

detecting an intensity of laser light originating from the object in a first detection direction parallel to the laser beam direction;

determining a first time, $\tau(0)$, and a second time, $\tau(2R_D)$, from the intensity of the laser light detected in the first detection direction, $\tau(0)$ being representative of the laser beam being tangential to the outer surface of the object at a first point of the object, and $\tau(2R_D)$ being representative of the laser beam being tangential to the outer surface of the object at a second point of the object diametrically opposite the first point;

detecting an intensity of laser light originating from the object in a second detection direction at a detection angle, $\alpha$, greater than zero to the first detection direction;

determining a third time, $\tau(x_{D2})$, and a fourth time, $\tau(x_{d2})$, from the intensity of the laser light detected in the second detection direction, $\tau(x_{D2})$ being representative of the laser beam being reflected at the outer surface of the object at a third point of the object, and $\tau(x_{d2})$ being representative of the laser beam being refracted at the outer surface of the object and reflected at the inner surface of the object at a fourth point of the object; and calculating an inner radius, $R_d$, of the object based on n, $v_s$, $\alpha$, $\tau(0)$, $\tau(2R_D)$, $\tau(x_{D2})$ and $\tau(x_{d2})$, wherein calculating $R_d$ includes calculating a difference between $\tau(2R_D)$ and $\tau(0)$, and a difference between $\tau(x_{d2})$ and $\tau(x_{D2})$.

Detecting laser light intensity includes detecting one or more distinct transitions of the intensity of the laser light, in particular:

an intensity transition from a high intensity (higher than a first high intensity threshold) to a low intensity (lower than the first high intensity threshold, or lower than a first low intensity threshold), or an intensity transition from a low intensity (lower than a second low intensity threshold) to a high intensity (higher than the second low intensity threshold, or higher than a second high intensity threshold), or a combination of an intensity transition from a low intensity (lower than a third low intensity threshold) to a high intensity (higher than the third low intensity threshold, or higher than a third high intensity threshold), and back to a low intensity (lower than the third high intensity threshold, or lower than the third low intensity threshold).

Any one of the first, second and third low intensity thresholds may be the same as or different from any other one of the first, second and third low intensity thresholds or any one of the first, second and third high intensity thresholds. Any one of the first, second and third high intensity thresholds may be the same as or different from any other one of the first, second and third high intensity thresholds or any one of the first, second and third low intensity thresholds.

According to the first include of the method of the disclosure, laser light intensity is detected in two distinct detection directions, i.e. a first detection direction and a second detection direction, as seen after the laser light has passed the tubular object. Detection of laser light intensity in the first detection direction provides the first time and the second time, and detection of laser light intensity in the second detection direction provides the third time and the fourth time.

In particular, the detections of laser light intensity in the first direction are used to calculate, by a processing system, a time difference between the second time and the first time, from which time difference an outer radius, $R_D$, of the tubular object can be derived. Since this time difference is relatively long, any inaccuracy in determining the first time and the second time plays a relatively minor role in the accuracy of the time difference value.

Also in particular, the detections of laser light intensity in the second direction are used to calculate, by a processing system, a time difference between the fourth time and the third time, which will be shorter when a difference between $R_D$ and $R_d$ decreases. However, this time difference will still be sufficient to provide an acceptable accuracy in determining the time difference between the fourth time and the third time.

As a result, the method provides an improved accuracy in a calculation of $R_d$ or, equivalently, the inner diameter of the object, based on the detected times when scanning the tubular object with a laser beam, in particular when the tubular object is thin.

The refraction index of the transparent material of the tubular object may be known, or may be unknown. In both circumstances, appropriate includes of the method may be applied to perform measurements of the tubular object to be able to calculate the inner radius thereof, as disclosed herein.

The result of the calculation may be a signal used to provide a value of $R_d$ at a user interface, such as a display unit. The signal may also be used to monitor or control a production line, or to control a device producing tubular objects.

It is noted here that the Jablonski et al. method proposes to use time differences between the third time and the first time, and between the fourth time and the first time. The second time, in the first detection direction, and a time difference between the fourth time and the third time are not used in the Jablonski et al. method.

In a second include of the method of the disclosure, a method for measuring a property of a transparent tubular object having a refractive index, n, and a longitudinal axis is provided. The second include of the method includes:

scanning a laser beam in a scanning direction with a constant scanning speed, $v_s$, along a scanning path at right angles to the longitudinal axis of the object, wherein the laser beam is directed at right angles to the longitudinal axis of the object, wherein the scanning laser beam is directed in a first laser beam direction to the object at right angles to the scanning direction in a first part of the scanning path, and redirected via a reflector in a second laser beam direction to the object at a scanning angle, $\beta$, greater than zero to the first laser beam direction in a second part of the scanning path;

detecting an intensity of laser light originating from the object in a first detection direction parallel to the first laser beam direction;

determining a first time, $\tau(0)$, and a second time, $\tau(2R_D)$, from the intensity of the laser light detected in the first detection direction, $\tau(0)$ being representative of the laser beam being tangential to the outer surface of the object at a first point of the object, and $\tau(2R_D)$ being representative of the laser beam being tangential to the outer surface of the object at a second point of the object diametrically opposite the first point;

detecting an intensity of laser light originating from the object in a second detection direction at a detection angle, $\alpha$, to the first detection direction;

determining a third time, $\tau(x_{D2})$, and a fourth time, $\tau(x_{d2})$, from the intensity of the laser light detected in the second detection direction, $\tau(x_{D2})$ being representative of the laser beam being reflected at the outer surface of the object at a third point of the object, and $\tau(x_{d2})$ being representative of the laser beam being refracted at the outer surface of the object and reflected at the inner surface of the object at a fourth point of the object; and calculating an inner radius, $R_d$, of the object based on n, $v_s$, α, β, τ(0), τ(2$R_D$), τ($x_{D2}$) and τ($x_{d2}$), wherein calculating $R_d$ includes calculating a difference between τ(2$R_D$) and τ(0), and a difference between τ($x_{d2}$) and τ($x_{D2}$).

In a third include of the method of the disclosure, a method for measuring a property of a transparent tubular object having a longitudinal axis is provided. The third include of the method includes:

scanning a laser beam in a scanning direction with a constant scanning speed, $v_s$, along a scanning path at right angles to the longitudinal axis of the object, wherein the scanning laser beam is directed in a first laser beam direction to the object at right angles to the scanning direction and at right angles to the longitudinal axis of the object;

detecting an intensity of laser light originating from the object in a first detection direction parallel to the first laser beam direction;

determining a first time, τ(0), and a second time, τ(2$R_D$), from the intensity of the laser light detected in the first detection direction, τ(0) being representative of the laser beam being tangential to the outer surface of the object at a first point of the object, and τ(2$R_D$) being representative of the laser beam being tangential to the outer surface of the object at a second point of the object diametrically opposite the first point;

detecting an intensity of laser light originating from the object in a second detection direction at a detection angle, a, greater than zero to the first detection direction;

determining a third time, τ($x_{D2}$), and a fourth time, τ($x_{d2}$), from the intensity of the laser light detected in the second detection direction, τ($x_{D2}$) being representative of the laser beam being reflected at the outer surface of the object at a third point of the object, and τ($x_{d2}$) being representative of the laser beam being refracted at the outer surface of the object and reflected at the inner surface of the object at a fourth point of the object;

determining a fifth time, τ($x_{d1}$), from the intensity of the laser light detected in the first detection direction, τ($x_{d1}$) being representative of the laser beam being refracted at the outer surface of the object and reflected at the inner surface of the object at a fifth point of the object; and calculating an inner radius, $R_d$, of the object based on $v_s$, α, τ(0), τ(2$R_D$), τ($x_{D2}$), τ($x_{d2}$) and τ($x_{d1}$), wherein calculating $R_d$ includes calculating a difference between τ(2$R_D$) and τ(0), and a difference between τ($x_{d2}$) and τ($x_{D2}$).

In a fourth include of a method according to the disclosure, a method for measuring a property of a transparent tubular object having a longitudinal axis is provided. The fourth include of the method includes:

scanning a laser beam in a scanning direction with a constant scanning speed, $v_s$, along a scanning path at right angles to the longitudinal axis of the object, wherein the laser beam is directed at right angles to the longitudinal axis of the object, wherein the scanning laser beam is directed in a first laser beam direction to the object at right angles to the scanning direction in a first part of the scanning path, and redirected via a reflector in a second laser beam direction to the object at a scanning angle, β, greater than zero to the first laser beam direction in a second part of the scanning path;

detecting an intensity of laser light originating from the object in a first detection direction parallel to the laser beam direction;

determining a first time, τ(0), and a second time, τ(2$R_D$), from the intensity of the laser light detected in the first detection direction, τ(0) being representative of the laser beam being tangential to the outer surface of the object at a first point of the object, and τ(2$R_D$) being representative of the laser beam being tangential to the outer surface of the object at a second point of the object diametrically opposite the first point;

detecting an intensity of laser light originating from the object in a second detection direction at a detection angle, α, to the first detection direction;

determining a third time, τ($x_{D2}$), and a fourth time, τ($x_{d2}$), from the intensity of the laser light detected in the second detection direction, τ($x_{D2}$) being representative of the laser beam being reflected at the outer surface of the object at a third point of the object, and τ($x_{d2}$) being representative of the laser beam being refracted at the outer surface of the object and reflected at the inner surface of the object at a fourth point of the object;

determining a fifth time, τ($x_{d1}$), from the intensity of the laser light detected in the first detection direction, τ($x_{d1}$) being representative of the laser beam being refracted at the outer surface of the object and reflected at the inner surface of the object at a fifth point of the object; and calculating an inner radius, $R_d$, of the object based on $v_s$, α, β, τ(0), τ(2$R_D$), τ($x_{D2}$), τ($x_{d2}$) and τ($x_{d1}$), wherein calculating $R_d$ includes calculating a difference between τ(2$R_D$) and τ(0), and a difference between τ($x_{d2}$) and τ($x_{D2}$).

In the third and fourth includes of the method, additionally measuring the fifth time in addition to the first, second, third and fourth times, the refractive index n can be eliminated from the calculation of $R_d$. This is an advantage, since n of the material of the tubular object does not need to be known beforehand.

In the first include of the method, wherein the first, second, third and fourth times are determined, wherein the detection angle α between the first detection direction and the second detection direction is 90°, and wherein the refractive index n of the tubular object is known, the inner radius $R_d$ of the tubular object is calculated based on the equation:

$$R_d = R_D \cdot \frac{1 - \frac{x_{d2}}{R_D}}{n \cdot \sin\left(\frac{\pi}{4} + \arcsin\left(\frac{1 - \frac{x_{d2}}{R_D}}{n}\right) - \arcsin\left(1 - \frac{x_{d2}}{R_D}\right)\right)},$$

wherein:

$$R_D = \frac{v_s}{2} \cdot (\tau(2R_D) - \tau(0))$$

and $$x_{d2} = R_D \cdot \left(\frac{2(\tau(x_{d2}) - \tau(x_{D2}))}{\tau(2R_D) - \tau(0)} + 1 - \sin(\pi/4)\right).$$

In the first include of the method, wherein the first, second, third and fourth times are determined, wherein the detection angle α between the first detection direction and the second detection direction may be different from 90°, and may be between 45° and 135°, and wherein the refractive index n of the tubular object is known, the inner radius $R_d$ of the tubular object is calculated based on the equation:

$$R_d = R_D \cdot \frac{1 - \frac{x_{d2}}{R_D}}{n \cdot \sin\left(\frac{\alpha}{2} + \arcsin\left(\frac{1 - \frac{x_{d2}}{R_D}}{n}\right) - \arcsin\left(1 - \frac{x_{d2}}{R_D}\right)\right)},$$

wherein:

$$R_D = \frac{v_s}{2} \cdot (\tau(2R_D) - \tau(0))$$

and $$x_{d2} = R_D \cdot \left( \frac{2(\tau(x_{d2}) - \tau(x_{D2}))}{\tau(2R_D) - \tau(0)} + 1 - \sin(\alpha/2) \right).$$

In the second include of the method, wherein the first, second, third and fourth times are determined, wherein the detection angle α between the first detection direction and the second detection direction may be different from 90°, and may be between 45° en 135°, wherein the sum of the detection angle α and the scanning angle β between the first laser beam direction and the second laser beam direction may be between 45° and 135°, and may be 90° in particular, and wherein the refractive index n of the tubular object is known, the inner radius $R_d$ of the tubular object is calculated based on the equation:

$$R_d = R_D \cdot \frac{1 - \frac{x_{d2}}{R_D}}{n \cdot \sin\left( \frac{\alpha + \beta}{2} + \arcsin\left( \frac{1 - \frac{x_{d2}}{R_D}}{n} \right) - \arcsin\left( 1 - \frac{x_{d2}}{R_D} \right) \right)},$$

wherein:

$$R_D = \frac{v_s}{2} \cdot (\tau(2R_D) - \tau(0))$$

and $$x_{d2} = R_D \cdot \left( \frac{2(\tau(x_{d2}) - \tau(x_{D2}))}{\tau(2R_D) - \tau(0)} + 1 - \sin((\alpha + \beta)/2) \right).$$

In the third include of the method, wherein the first, second, third, fourth and fifth times are determined, wherein the detection angle α between the first detection direction and the second detection direction is 90°, and wherein the refractive index n of the tubular object is not known, the inner radius $R_d$ of the tubular object is calculated based on the equation:

$$R_d = R_D \frac{1}{b + \sqrt{b^2 - 1}}$$

wherein:

$$R_D = \frac{v_s}{2} \cdot (\tau(2R_D) - \tau(0)),$$

$$b = \frac{g\sin\beta_1 - \cos\left(\frac{\pi}{4} - \beta_2\right)}{g - 1},$$

$$g = \left( \tan\beta_1 \frac{\sin\left(\frac{\pi}{4} - \beta_2\right)}{\sin\beta_2} \right)^2,$$

$$\beta_1 = \arcsin\left(1 - \frac{x_{d1}}{R_D}\right),$$

$$\beta_2 = \arcsin\left(1 - \frac{x_{d2}}{R_D}\right),$$

$$x_{d1} = v_s \cdot (\tau(x_{d1}) - \tau(0)) = 2 \cdot R_d \cdot \frac{(\tau(x_{d1}) - \tau(0))}{(\tau(2R_D) - \tau(0))},$$

and $$x_{d2} = R_D \cdot \left( \frac{2(\tau(x_{d2}) - \tau(x_{D2}))}{\tau(2R_D) - \tau(0)} + 1 - \sin(\pi/4) \right).$$

In the third include of the method, wherein the first, second, third, fourth and fifth times are determined, wherein the detection angle α between the first detection direction and the second detection direction may be different from 90°, and may be between 45° and 135°, and wherein the refractive index n of the tubular object is not known, the inner radius $R_d$ of the tubular object is calculated based on the equation:

$$R_d = R_D \frac{1}{b + \sqrt{b^2 - 1}}$$

wherein:

$$R_D = \frac{v_s}{2} \cdot (\tau(2R_D) - \tau(0)),$$

$$b = \frac{g\sin\beta_1 - \cos\left(\frac{\alpha}{2} - \beta_2\right)}{g - 1},$$

$$g = \left( \tan\beta_1 \frac{\sin\left(\frac{\alpha}{2} - \beta_2\right)}{\sin\beta_2} \right)^2,$$

$$\beta_1 = \arcsin\left(1 - \frac{x_{d1}}{R_D}\right),$$

$$\beta_2 = \arcsin\left(1 - \frac{x_{d2}}{R_D}\right),$$

$$x_{d1} = v_s \cdot (\tau(x_{d1}) - \tau(0)) = 2 \cdot R_d \cdot \frac{(\tau(x_{d1}) - \tau(0))}{(\tau(2R_D) - \tau(0))},$$

and $$x_{d2} = R_D \cdot \left( \frac{2(\tau(x_{d2}) - \tau(x_{D2}))}{\tau(2R_D) - \tau(0)} + 1 - \sin(\alpha/2) \right).$$

In the fourth include of the method, wherein the first, second, third, fourth and fifth times are determined, wherein the detection angle α between the first detection direction and the second detection direction may be different from 90°, and may be between 45° and 135°, wherein the sum of the detection angle α and the scanning angle β between the first laser beam direction and the second laser beam direction may be between 45° and 135°, and may be 90° in particular, and wherein the refractive index n of the tubular object is not known, the inner radius $R_d$ of the tubular object is calculated based on the equation:

$$R_d = R_D \frac{1}{b + \sqrt{b^2 - 1}}$$

wherein:

$$R_D = \frac{v_s}{2} \cdot (\tau(2R_D) - \tau(0)),$$

-continued $$b = \frac{g\sin\beta_1 - \cos\left(\frac{\alpha+\beta}{2} - \beta_2\right)}{g - 1},$$

$$g = \left(\tan\beta_1 \frac{\sin\left(\frac{\alpha+\beta}{2} - \beta_2\right)}{\sin\beta_2}\right)^2,$$

$$\beta_1 = \arcsin\left(1 - \frac{x_{d1}}{R_D}\right),$$

$$\beta_2 = \arcsin\left(1 - \frac{x_{d2}}{R_D}\right),$$

$$x_{d1} = v_s \cdot (\tau(x_{d1}) - \tau(0)) = 2 \cdot R_d \cdot \frac{(\tau(x_{d1}) - \tau(0))}{(\tau(2R_D) - \tau(0))},$$

and $$x_{d2} = R_D \cdot \left(\frac{2(\tau(x_{d2}) - \tau(x_{D2}))}{\tau(2R_D) - \tau(0)} + 1 - \sin((\alpha + \beta)/2)\right).$$

In an include of the first, second, third and fourth include of the method of the disclosure, the method further includes:

polarizing the scanning laser beam in a 45° polarizing direction; and polarizing the laser light originating from the object in the first detection direction in a (−45+δ)° polarizing direction, wherein |δ|>0; and/or polarizing the laser light originating from the object in the second detection direction in a (45+ε)° polarizing direction, wherein |ε|>0.

An advantage of polarizing the laser light in the indicated way is that, in the first detection direction, the intensities of the fully transmitted laser beam outside the tubular object and the laser light transmitted inside the tubular object, can be balanced by adjusting the angle δ. Also, in the second detection direction, the intensities of the laser light directly reflected at the outer surface of the tubular object and the laser light reflected at the inner surface of the tubular object, can be balanced by adjusting the angle E.

In some includes, the step of polarizing the laser light originating from the object in the first detection direction in a (−45+δ)° polarizing direction is omitted and the step of polarizing the laser light originating from the object in the second detection direction in a (45+ε)° polarizing direction is performed. In other includes, the step of polarizing the laser light originating from the object in the first detection direction in a (−45+δ)° polarizing direction is performed and the step of polarizing the laser light originating from the object in the second detection direction in a (45+ε)° polarizing direction is omitted. In still other includes, both the step of polarizing the laser light originating from the object in the first detection direction in a (−45+δ)° polarizing direction, and the step of polarizing the laser light originating from the object in the second detection direction in a (45+ε)° polarizing direction are performed.

In a second aspect of the disclosure, a first, second, third and fourth apparatus for measuring a property of a transparent tubular object having a refractive index, n, and a longitudinal axis are provided. The first include of the apparatus includes:

a laser beam scanner configured for scanning a laser beam in a scanning direction with a constant scanning speed, $v_s$, along a scanning path at right angles to the longitudinal axis of the object, wherein the scanning laser beam is directed in a first laser beam direction to the object at right angles to the scanning direction and at right angles to the longitudinal axis of the object;

a detector configured for detecting an intensity of laser light originating from the object in a first detection direction parallel to the first laser beam direction, and for detecting an intensity of laser light originating from the object in a second detection direction at a detection angle, a, greater than zero to the first detection direction; and a processing system configured for:

determining a first time, τ(0), and a second time, τ(2R$_D$), from the intensity of the laser light detected in the first detection direction by the detector, τ(0) being representative of the laser beam being tangential to the outer surface of the object at a first point of the object, and τ(2R$_D$) being representative of the laser beam being tangential to the outer surface of the object at a second point of the object diametrically opposite the first point;

determining a third time, τ(x$_{D2}$), and a fourth time, τ(x$_{d2}$), from the intensity of the laser light detected in the second detection direction by the detector, τ(x$_{D2}$) being representative of the laser beam being reflected at the outer surface of the object at a third point of the object, and τ(x$_{d2}$) being representative of the laser beam being refracted at the outer surface of the object and reflected at the inner surface of the object at a fourth point of the object; and calculating an inner radius, R$_d$, of the object based on n, $v_s$, a, τ(0), τ(2R$_D$), τ(x$_{D2}$), and τ(x$_{d2}$), wherein calculating R$_d$ includes calculating a difference between τ(2R$_D$) and τ(0), and a difference between τ(x$_{d2}$) and τ(x$_{D2}$).

According to the first include of the apparatus of the disclosure, in the apparatus laser light intensity is detected in two distinct detection directions, i.e. a first detection direction and a second detection direction, as seen after the laser light has passed the tubular object. Detection of laser light intensity in the first detection direction by the detector assembly provides the first time and the second time, and detection of laser light intensity in the second detection direction by the detector assembly provides the third time and the fourth time.

In particular, the detections of laser light intensity in the first direction by the detector assembly are used to calculate a time difference between the second time and the first time by the processing system for calculating R$_D$ by the processing system. Since this time difference is relatively long, any inaccuracy in determining the first time and the second time plays a relatively minor role in the time difference value.

Also in particular, the detections of laser light intensity in the second direction by the detector assembly are used to calculate a time difference between the fourth time and the third time by the processing system, which time difference will be shorter when a difference between R$_D$ and R$_d$ decreases. So, also here, in particular when thin tubular objects are measured, any inaccuracy in determining the third time and the fourth time plays a decreasing role in the time difference value.

As a result, the apparatus provides an improved accuracy in a calculation of the R$_d$ based on the detected times when scanning the tubular object with the laser beam, in particular when the tubular object is thin.

In a second include of an apparatus according to the disclosure, an apparatus for measuring a property of a transparent tubular object having a refractive index, n, and a longitudinal axis is provided. The second include of the apparatus includes:

a laser beam scanner configured for scanning a laser beam in a scanning direction with a constant scanning speed, $v_s$, along a scanning path at right angles to the longitudinal axis of the object, wherein the scanning laser beam is directed at right angles to the longitudinal axis of the object, wherein the scanning laser beam is directed in a first laser beam direction to the object at right angles to the scanning direction in a first part of the scanning path, and redirected via a reflector in a second laser beam direction to the object at a scanning angle, β, greater than zero to the first laser beam direction in a second part of the scanning path;

a detector assembly configured for detecting an intensity of laser light originating from the object in a first detection direction parallel to the first laser beam direction, and configured for detecting an intensity of laser light originating from the object in a second detection direction at a detection angle, a, to the first detection direction; and a processing system configured for:
  determining a first time, $\tau(0)$, and a second time, $\tau(2R_D)$, from the intensity of the laser light detected in the first detection direction, $\tau(0)$ being representative of the laser beam being tangential to the outer surface of the object at a first point of the object, and $\tau(2R_D)$ being representative of the laser beam being tangential to the outer surface of the object at a second point of the object diametrically opposite the first point;
  determining a third time, $\tau(x_{D2})$, and a fourth time, $\tau(x_{d2})$, from the intensity of the laser light detected in the second detection direction, $\tau(x_{D2})$ being representative of the laser beam being reflected at the outer surface of the object at a third point of the object, and $\tau(x_{d2})$ being representative of the laser beam being refracted at the outer surface of the object and reflected at the inner surface of the object at a fourth point of the object; and
  calculating an inner radius, $R_d$, of the object based on n, $v_s$, a, β, $\tau(0)$, $\tau(2R_D)$, $\tau(x_{D2})$ and $\tau(x_{d2})$, wherein calculating $R_d$ includes calculating a difference between $\tau(2R_D)$ and $\tau(0)$, and a difference between $\tau(x_{d2})$ and $\tau(x_{D2})$.

In a third include of an apparatus according to the disclosure, an apparatus for measuring a property of a transparent tubular object having a longitudinal axis is provided. The third include of the apparatus includes:

a laser beam scanner configured for scanning a laser beam in a scanning direction with a constant scanning speed, $v_s$, along a scanning path at right angles to the longitudinal axis of the object, wherein the scanning laser beam is directed in a first laser beam direction to the object at right angles to the scanning direction and at right angles to the longitudinal axis of the object;

a detector assembly configured for detecting an intensity of laser light originating from the object in a first detection direction parallel to the first laser beam direction, and detecting an intensity of laser light originating from the object in a second detection direction at a detection angle, a, greater than zero to the first detection direction; and a processing system configured for:
  determining a first time, $\tau(0)$, and a second time, $\tau(2R_D)$, from the intensity of the laser light detected in the first detection direction, $\tau(0)$ being representative of the laser beam being tangential to the outer surface of the object at a first point of the object, and $\tau(2R_D)$ being representative of the laser beam being tangential to the outer surface of the object at a second point of the object diametrically opposite the first point;
  determining a third time, $\tau(x_{D2})$, and a fourth time, $\tau(x_{d2})$, from the intensity of the laser light detected in the second detection direction, $\tau(x_{D2})$ being representative of the laser beam being reflected at the outer surface of the object at a third point of the object, and $\tau(x_{d2})$ being representative of the laser beam being refracted at the outer surface of the object and reflected at the inner surface of the object at a fourth point of the object;
  determining a fifth time, $\tau(x_{d1})$, from the intensity of the laser light detected in the first detection direction, $\tau(x_{d1})$ being representative of the laser beam being refracted at the outer surface of the object and reflected at the inner surface of the object at a fifth point of the object; and
  calculating an inner radius, $R_d$, of the object based on $v_s$, a, $\tau(0)$, $\tau(2R_D)$, $\tau(x_{D2})$, $\tau(x_{d2})$ and $\tau(x_{d1})$, wherein calculating $R_d$ includes calculating a difference between $\tau(2R_D)$ and $\tau(0)$, and a difference between $\tau(x_{d2})$ and $\tau(x_{D2})$.

In a fourth include of an apparatus according to the disclosure, an apparatus for measuring a property of a transparent tubular object having a longitudinal axis is provided. The fourth include of the apparatus includes:

a laser beam scanner configured for scanning a laser beam in a scanning direction with a constant scanning speed, $v_s$, along a scanning path at right angles to the longitudinal axis of the object, wherein the laser beam is directed at right angles to the longitudinal axis of the object, wherein the scanning laser beam is directed in a first laser beam direction to the object at right angles to the scanning direction in a first part of the scanning path, and redirected via a reflector in a second laser beam direction to the object at a scanning angle, β, greater than zero to the first laser beam direction in a second part of the scanning path;

a detector assembly configured for detecting an intensity of laser light originating from the object in a first detection direction parallel to the laser beam direction, and detecting an intensity of laser light originating from the object in a second detection direction at a detection angle, a, to the first detection direction; and a processing system configured for:
  determining a first time, $\tau(0)$, and a second time, $\tau(2R_D)$, from the intensity of the laser light detected in the first detection direction, $\tau(0)$ being representative of the laser beam being tangential to the outer surface of the object at a first point of the object, and $\tau(2R_D)$ being representative of the laser beam being tangential to the outer surface of the object at a second point of the object diametrically opposite the first point;
  determining a third time, $\tau(x_{D2})$, and a fourth time, $\tau(x_{d2})$, from the intensity of the laser light detected in the second detection direction, $\tau(x_{D2})$ being representative of the laser beam being reflected at the outer surface of the object at a third point of the object, and $\tau(x_{d2})$ being representative of the laser beam being refracted at the outer surface of the object and reflected at the inner surface of the object at a fourth point of the object;
  determining a fifth time, $\tau(x_{d1})$, from the intensity of the laser light detected in the first detection direction, $\tau(x_{d1})$ being representative of the laser beam being refracted at the outer surface of the object and reflected at the inner surface of the object at a fifth point of the object; and
  calculating an inner radius, $R_d$, of the object based on $v_s$, a, β, $\tau(0)$, $\tau(2R_D)$, $\tau(x_{D2})$, $\tau(x_{d2})$ and $\tau(x_{d1})$, wherein calculating $R_d$ includes calculating a difference between $\tau(2R_D)$ and $\tau(0)$, and a difference between $\tau(x_{d2})$ and $\tau(x_{D2})$.

A value representing $R_d$ or, equivalently, the inner diameter, of the tubular object may be output by the processing system in a suitable form, e.g. as a signal.

With the third and fourth includes of the apparatus, additionally measuring the fifth time by the detector assembly in addition to the first, second, third and fourth times, the refractive index n may be eliminated from the equations underlying the calculation of $R_d$, and $R_d$ may be calculated by the processing system. This is an advantage, since n of the material of the tubular object does not need to be known beforehand.

In the first and third includes of the apparatus, the detection angle α between the first detection direction and the second detection direction is between 45° and 135°.

Preferably, the detection angle is 90° in the detector assembly, since such an arrangement allows for a relatively simple arrangement of the detector assembly and fast calculation by the processing system of $R_d$. However, other angles, such as angles between 45° and 135°, are also possible, and may provide an improved sensitivity for $R_d$.

In the second and fourth includes of the apparatus, the detection angle α between the first detection direction and the second detection direction may be 0°. The scanning angle β between the first laser beam direction and the second laser beam direction may be between 45° and 135°, wherein preferably the sum of α and β is between 45° and 135°.

In an include of the first, second, third and fourth includes of the apparatus of the present disclosure, the detector assembly includes:
  a first detector configured for detecting the intensity of laser light originating from the object in the first detection direction; and
  a second detector, different from the first detector, and configured for detecting the intensity of laser light originating from the object in the second detection direction.

An advantage of having separate detectors is that they may be positionable relative to each other to obtain an optimum measurement of one or more particular tubular objects. Also, an angular position of the second detector may be set to be in a predetermined second detection direction providing an optimum sensitivity of the measurement.

In an include of the apparatus having separate detectors, the detector assembly further includes:
  a reflector arranged between the object and the second detector, the reflector being configured for reflecting laser light originating from the object in the second detection direction towards the second detector.

By appropriately positioning the reflector, both with regard to its position relative to the object and with regard to its angle of incidence and angle of reflection of the laser light, an optimum sensitivity of the measurement can be achieved in a simple way.

In an include of the apparatus having separate detectors and a reflector, the reflector is configured for reflecting laser light originating from the object in the second detection direction to be in the first detection direction. In this include, the apparatus may further include:
  a laser beam polarizer arranged between the laser beam scanner and the object, the polarizer being configured for polarizing the laser beam;
  a waveplate, in particular a half-lambda plate, arranged between the object and the reflector, the half-lambda plate being configured for rotating the polarization direction of the laser light originating from the object; and
  a polarizing beam splitter arranged and configured for splitting the laser light from the object and the reflector in the first detection direction, to the first detector and the second detector based on the polarization state of the laser light.

In practice, in the detector assembly, each one of the first detector and second detector is combined with a condenser lens to focus the laser light in the first detection direction and in the second detection direction, respectively. The laser beam polarizer, waveplate and polarizing beam splitter allow the use of one condenser lens for both the first and the second detector.

In another include of the first, second, third and fourth includes of the apparatus of the present disclosure, the detector assembly includes:
  a reflector for reflecting laser light originating from the object in the second detection direction to be in the first detection direction; and
  a first detector configured for detecting the intensity of laser light originating from the object in the first detection direction, and configured for detecting the intensity of laser light originating from the object in the second detection direction and being reflected by the reflector to be in the first detection direction.

A feature of having only one first laser light detector is the simplicity of the arrangement, and the omission of a second detector, which makes the apparatus less costly, since the light detectors are relatively expensive. On the other hand, the reflector is a relatively low-cost component. Only one condenser lens needs to be used to focus the laser light from the tubular object, both directly from the tubular object in the first detection direction and from the reflector in the first detection direction, on the first detector.

In an include of the apparatus including a reflector, the reflector includes a pentagon prism or a mirror.

A pentagon prism and a mirror provide suitable reflectors to reflect light rays incident on the pentagon prism or mirror in the second detection direction at different angles, depending on the desired angle between the first detection direction and the second detection direction. The pentagon prism may ensure that the light in the second detection direction is 90° to the light in the first detection direction, although pentagon prisms may be configured to reflect light at other angles than 90°.

In the first include of the apparatus of the disclosure, the processing system is configured to calculate the inner radius $R_d$ based on the following equation, wherein the first, second, third and fourth times are determined by the processing system, wherein the detection angle α between the first detection direction and the second detection direction is or has been measured, or is known, and may be between 45° and 135°, preferably 90°, and wherein the refractive index n of the tubular object is known:

$$R_d = R_D \cdot \frac{1 - \frac{x_{d2}}{R_D}}{n \cdot \sin\left(\frac{\alpha}{2} + \arcsin\left(\frac{1 - \frac{x_{d2}}{R_D}}{n}\right) - \arcsin\left(1 - \frac{x_{d2}}{R_D}\right)\right)},$$

wherein:

$$R_D = \frac{v_s}{2} \cdot (\tau(2R_D) - \tau(0))$$

and

-continued $$x_{d2} = R_D \cdot \left(\frac{2(\tau(x_{d2}) - \tau(x_{D2}))}{\tau(2R_D) - \tau(0)} + 1 - \sin(\alpha/2)\right).$$

In the second include of the apparatus of the disclosure, the processing system is configured to calculate the inner radius $R_d$ based on the following equation, wherein the first, second, third and fourth times are determined by the processing system, wherein the detection angle α between the first detection direction and the second detection direction is or has been measured, or is known, and may be 0° or different from 0°, wherein the scanning angle β between the first laser beam direction and the second laser beam direction is or has been measured, or is known, and may be between 45° and 135°, preferably 90°, wherein the sum of α and β preferably is between 45° and 135°, and wherein the refractive index n of the tubular object is known:

$$R_d = R_D \cdot \frac{1 - \frac{x_{d2}}{R_D}}{n \cdot \sin\left(\frac{\alpha+\beta}{2} + \arcsin\left(\frac{1 - \frac{x_{d2}}{R_D}}{n}\right) - \arcsin\left(1 - \frac{x_{d2}}{R_D}\right)\right)},$$

wherein:

$$R_D = \frac{v_s}{2} \cdot (\tau(2R_D) - \tau(0))$$

and $$x_{d2} = R_D \cdot \left(\frac{2(\tau(x_{d2}) - \tau(x_{D2}))}{\tau(2R_D) - \tau(0)} + 1 - \sin((\alpha+\beta)/2)\right).$$

In the third include of the apparatus of the disclosure, the processing system is configured to calculate the inner radius $R_d$ based on the following equation, wherein the first, second, third, fourth and fifth times are determined by the processing system, wherein the detection angle α between the first detection direction and the second detection direction is or has been measured, or is known, and may be between 45° and 135°, preferably 90°, and wherein the refractive index n of the tubular object is not known:

$$R_d = R_D \frac{1}{b + \sqrt{b^2 - 1}}$$

wherein:

$$R_D = \frac{v_s}{2} \cdot (\tau(2R_D) - \tau(0)),$$

$$b = \frac{g\sin\beta_1 - \cos\left(\frac{\alpha}{2} - \beta_2\right)}{g - 1},$$

$$g = \left(\tan\beta_1 \frac{\sin\left(\frac{\alpha}{2} - \beta_2\right)}{\sin\beta_2}\right)^2,$$

$$\beta_1 = \arcsin\left(1 - \frac{x_{d1}}{R_D}\right),$$

$$\beta_2 = \arcsin\left(1 - \frac{x_{d2}}{R_D}\right),$$

$$x_{d1} = v_s \cdot (\tau(x_{d1}) - \tau(0)) = 2 \cdot R_d \cdot \frac{(\tau(x_{d1}) - \tau(0))}{(\tau(2R_D) - \tau(0))},$$

and $$x_{d2} = R_D \cdot \left(\frac{2(\tau(x_{d2}) - \tau(x_{D2}))}{\tau(2R_D) - \tau(0)} + 1 - \sin(\alpha/2)\right).$$

In the fourth include of the apparatus of the disclosure, the processing system is configured to calculate the inner radius $R_d$ based on the following equation, wherein the first, second, third, fourth and fifth times are determined by the processing system, wherein the detection angle α between the first detection direction and the second detection direction is or has been measured, or is known, and may be 0° or may be different from 0°, wherein the scanning angle β between the first laser beam direction and the second laser beam direction is or has been measured, or is known, and may be between 45° and 135°, preferably 90°, wherein the sum of α and β preferably is between 45° and 135°, and wherein the refractive index n of the tubular object is not known:

$$R_d = R_D \frac{1}{b + \sqrt{b^2 - 1}}$$

wherein:

$$R_D = \frac{v_s}{2} \cdot (\tau(2R_D) - \tau(0)),$$

$$b = \frac{g\sin\beta_1 - \cos\left(\frac{\alpha+\beta}{2} - \beta_2\right)}{g - 1},$$

$$g = \left(\tan\beta_1 \frac{\sin\left(\frac{\alpha+\beta}{2} - \beta_2\right)}{\sin\beta_2}\right)^2,$$

$$\beta_1 = \arcsin\left(1 - \frac{x_{d1}}{R_D}\right),$$

$$\beta_2 = \arcsin\left(1 - \frac{x_{d2}}{R_D}\right),$$

$$x_{d1} = v_s \cdot (\tau(x_{d1}) - \tau(0)) = 2 \cdot R_d \cdot \frac{(\tau(x_{d1}) - \tau(0))}{(\tau(2R_D) - \tau(0))},$$

and $$x_{d2} = R_D \cdot \left(\frac{2(\tau(x_{d2}) - \tau(x_{D2}))}{\tau(2R_D) - \tau(0)} + 1 - \sin((\alpha+\beta)/2)\right).$$

In an include, the apparatus further includes:

a first polarizer having a 45° polarizing direction, and being arranged in the path of the laser beam;

a second polarizer having a (−45+δ)° polarizing direction, and being arranged in the path of the laser light originating from the object in the first detection direction, wherein |δ|>0; and a third polarizer having a (45+ε)° polarizing direction, and being arranged in the path of the laser light originating from the object in the second detection direction, wherein |ε|>0.

These and other aspects of the invention will be more readily appreciated as the same becomes better understood by reference to the following detailed description and considered in connection with the accompanying drawings in which like reference symbols designate like parts.

DETAILED DESCRIPTION OF INCLUDES

The particulars shown herein are by way of example and for purposes of illustrative discussion of the includes of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the forms of the present invention may be embodied in practice.

Figure 1:
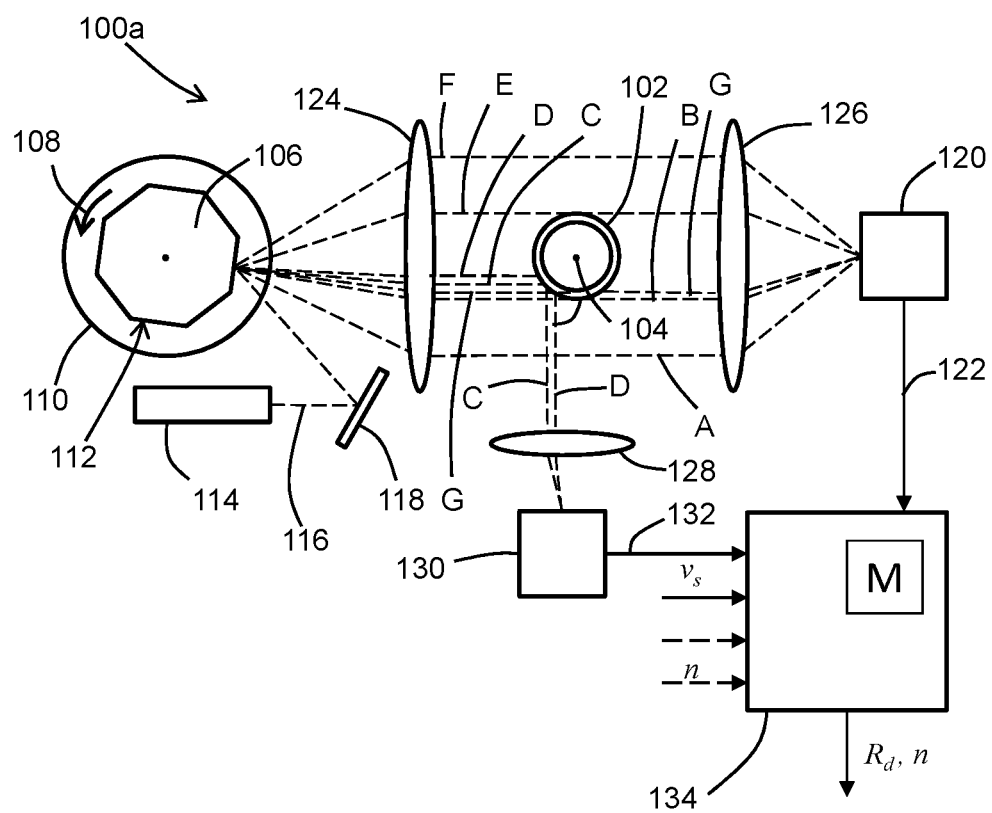
FIG. 1 schematically and diagrammatically depicts a first include of an apparatus according to the disclosure for measuring a property of a transparent tubular object.

Referring to the drawings wherein like characters represent like elements, FIG. 1 depicts a first include of an apparatus 100a for measuring a property, such as an inner radius or a refractive index, of a transparent tubular object 102, or tube, of which the dimensions are defined by an outer radius $R_D$ or outer diameter $2 \cdot R_D$ and inner radius $R_d$ or inner diameter $2 \cdot R_d$. The tubular object 102 has a longitudinal axis 104 extending at right angles to the plane of drawing of FIG. 1. It is noted here that the tubular object 102 does not form part of the apparatus for measuring a property thereof, and that any reference to the tubular object 102 when defining a location in the apparatus is to be taken as an envisaged position of the tubular object 102.

The apparatus 100a includes a frame structure which is not shown in FIG. 1, so as not to obscure the arrangement of some main components of the apparatus which are shown in FIG. 1, and which are supported in the frame structure so as to be adjustable to different tubular objects to be measured. The apparatus 100a includes a mirror assembly 106 being rotatable, as indicated by arrow 108, by a driving device 110. The mirror assembly 106 includes a plurality of (in the include shown: eight) reflecting planes 112. The apparatus 100a further includes a laser beam generator 114 configured for producing a laser beam 116 as indicated by a dashed line. A mirror 118 is arranged to reflect the laser beam 116 to the mirror assembly 106. It is noted here that the mirror 118 may be omitted, and the laser beam 116 can also be directed to the mirror assembly 106 directly. The combination of elements configured to produce the scanning laser beam can also be referred to as a laser beam scanner. Other includes of a laser beam scanner are also envisaged.

When the mirror assembly 106 is rotated with a predetermined constant rotational speed, the laser beam 116 reflected by any one of the reflecting planes 112 of the mirror assembly 106 is scanned in a scanning direction along a scanning path along a collimator lens 124 to generate a light strip extending between laser beam positions A and F from the collimator lens 124 to a first condenser lens 126. The scanning path and the scanning direction are at right angles to the longitudinal axis of the tubular object 102. The scanning laser beam is directed in a first laser beam direction to the object at right angles to the scanning direction and at right angles to the longitudinal axis of the tubular object 102. The first condenser lens 126 focuses the scanning light beam on a first light detector 120.

The first light detector 120 is configured to measure light intensity of the laser beam arriving at the first condenser lens 126 in a first detection direction at right angles both to the longitudinal axis of the tubular object and to the scanning direction of the laser beam, and to produce a first output signal 122 representative of the light intensity measured by the first light detector as a function of time.

The tubular object 102 is (to be) arranged in the light strip between the collimator lens 124 and the first condenser lens 126, with the longitudinal axis 104 of the tubular object 102 being at right angles to the laser beam direction originating from the collimator lens 124, and the longitudinal axis 104 of the tubular object 102 being at right angles to the scanning direction of the laser beam. The tubular object 102 may be supported or held by a support structure (not shown). The support structure may be adaptable or adjustable to different sizes of tubular objects 102.

Laser beams from laser beam position A to laser beam position B are not interrupted, refracted, reflected, or transmitted by the tubular object 102, and arrive at the first light detector 120. At laser beam position B, the laser beam tangentially passes the outer surface of the tubular object 102 at a first point P1 (see FIG. 11a) of the outer surface thereof.

Also from laser beam position E to laser beam position F, laser beams are not interrupted, refracted, reflected, or transmitted by the tubular object 102, and arrive at the first light detector 120. At laser beam position E, the laser beam tangentially passes the outer surface of the tubular object 102 at a second point P2 (see FIG. 11a) of the outer surface thereof diametrically opposite to the first point.

Laser beams between laser beam position B and laser beam position E are interrupted, refracted, reflected and/or transmitted by the tubular object 102. Interruptions are occasioned by reflections that lead the laser beams outside the numerical aperture of the first condenser lens 126. Refraction takes place at the outer surface and the inner surface of the tubular object 102. Reflection occurs at the outer surface and the inner surface of the tubular object 102. The laser beam crossing the longitudinal axis 104 of the tubular object 102 is transmitted through the tubular object 102.

A laser beam at laser beam position C is reflected against the outer surface of the tubular object 102 at a third point P3 (see FIG. 11a), and originates from the tubular object 102 in a second detection direction at right angles (i.e. at a detection angle α of 90°) to the first detection direction.

A laser beam at laser beam position D is refracted at the outer surface of the tubular object 102, reflected in the tubular object 102 against the inner surface of the tubular object 102 at a fourth point P4 (see FIG. 11a), and refracted again at the outer surface of the tubular object 102 in the second detection direction at right angles (i.e. at a detection angle α of 90°) to the first detection direction. A second condenser lens 128 focuses the laser light at laser beam positions C and D on a second light detector 130.

A laser beam at laser beam position G is refracted at the outer surface of the tubular object 102, reflected in the tubular object 102 against the inner surface of the tubular object 102 at a fifth point P5 (see FIG. 11a), and refracted again at the outer surface of the tubular object 102 in the first detection direction. The first condenser lens 126 focuses the laser light at laser beam position G on the first light detector 120.

The second light detector 130 is configured to measure light intensity, and to produce a second output signal 132 representative of the light intensity measured by the second light detector 130 as a function of time.

Together, the first light detector 120 and the second light detector 130 are part of a detector assembly, which may further include first condenser lens 126 and second condenser lens 128, and further optics such as one or more mirrors or prisms.

The first output signal 122 from the first light detector 120 and the second output signal 132 from the second light detector 130 are input to a processing system (processor) 134.

Furthermore, a signal representative of the scanning speed $v_s$ of the scanning laser beam produced by the rotating mirror assembly 106 may be input to the processing system, as indicated. In other includes, the scanning speed $v_s$ produced by the rotating mirror assembly 106 may be predetermined and stored in a memory M of the processing system 134. In still other includes, the rotational speed of the mirror assembly 106 may be predetermined and stored in one or more memories M of the processing system 134, and the processing system 134 controls the driving device 110 to cause the scanning laser beam to have the scanning speed $v_s$.

Furthermore, a signal representative of the detection angle α may be input to the processing system. In other includes, the detection angle α may be predetermined and stored in the memory M of the processing system 134.

Furthermore, a signal representative of the refractive index n of the material constituting the tubular object 102 may be input to the processing system. In other includes, the refractive index n of the material constituting the tubular object 102 may be predetermined and stored in the memory M of the processing system 134. In still other includes, the refractive index n of the material constituting the tubular object may be calculated from the light intensities represented in the first output signal 122 and the second output signal 132, as explained below.

The operation of the processing system 134 is explained below by reference to FIG. 11a.

Figure 2:
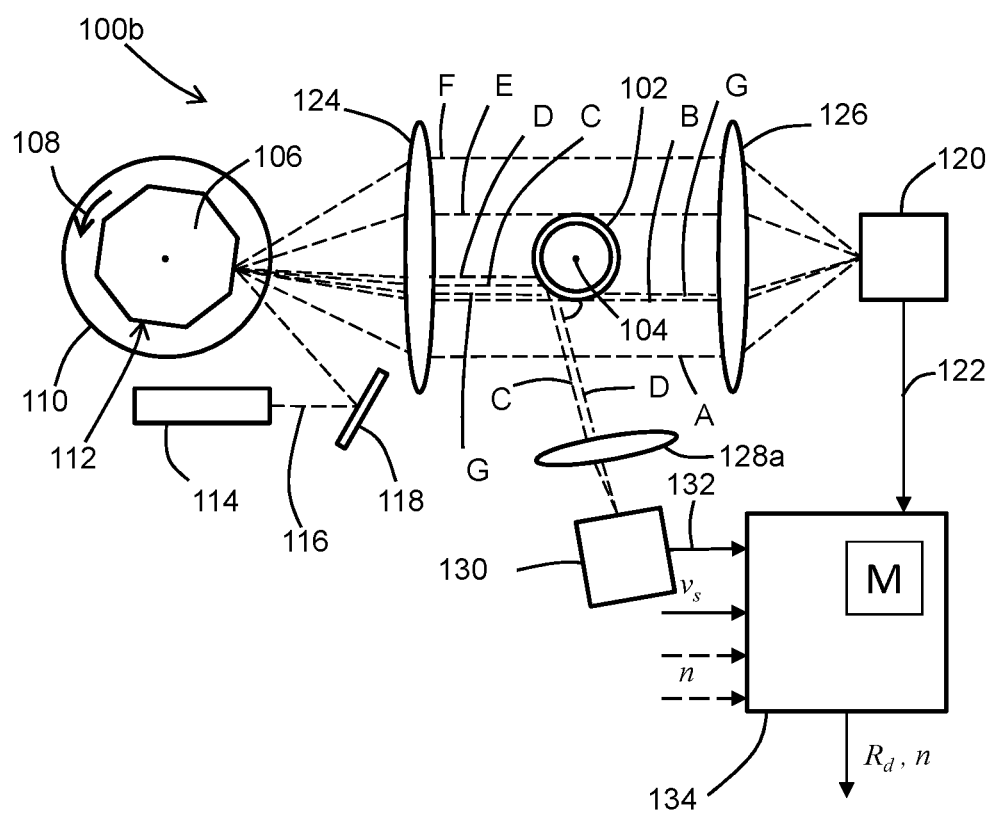
FIG. 2 schematically and diagrammatically depicts a second include of an apparatus according to the disclosure for measuring a property of a transparent tubular object.

FIG. 2 depicts a second include of an apparatus 100b for measuring a property, such as an inner radius or a refractive index, of a transparent tubular object 102, or tube, of which the dimensions are defined by an outer radius $R_D$ and inner radius $R_d$. In FIG. 2, the same reference signs as in FIG. 1 denote the same components, having the same or a similar function.

The apparatus 100b according to FIG. 2 differs from the apparatus 100a according to FIG. 1 in that the second detection direction of laser light is not at right angles to the first detection direction, but at a detection angle α different from 90°, in particular between 45° and 135° (in FIG. 2, about 105°). Such an arrangement is particularly useful when often tubular objects 102 with substantially the same outer radius $R_D$ and substantially the same inner radius $R_d$ are measured. The detection angle α between the first detection direction and the second detection direction can then be selected to have an optimum sensitivity for the inner radius $R_d$. Accordingly, the second condenser lens 128a and the second light detector 130 take a different position with respect to the tubular object 102. In the frame structure of the apparatus 100b, the position of the second condenser lens 128a and the second light detector 130 may be adjustable for adjusting the detection angle α.

Figure 3:
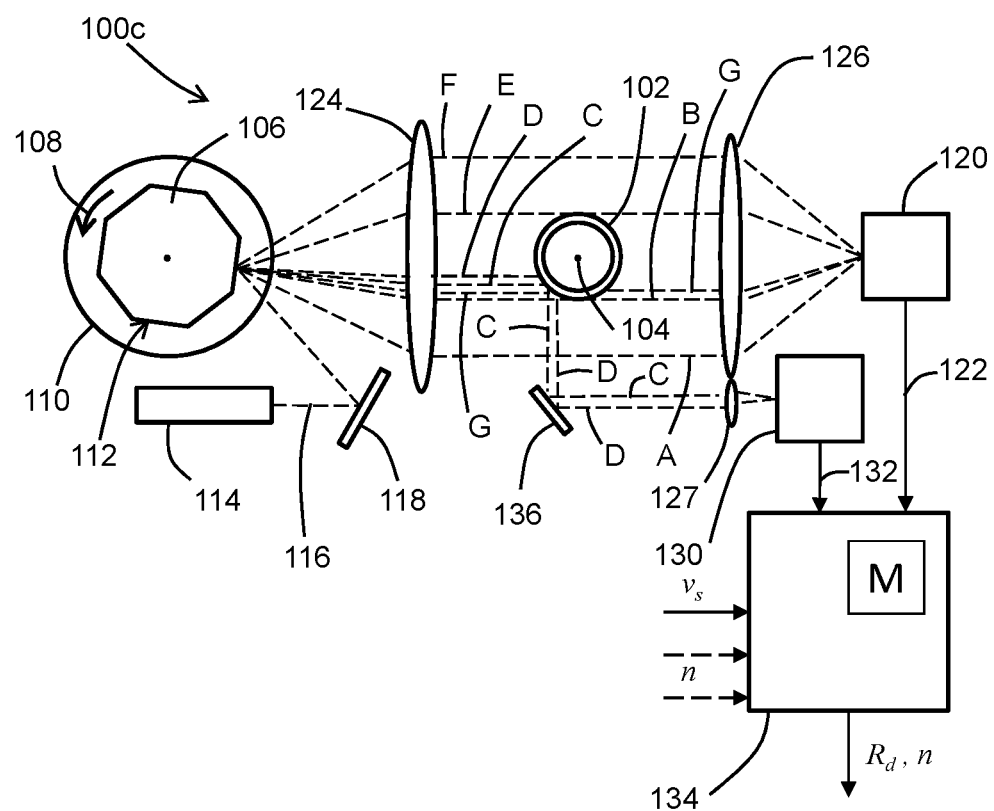
FIG. 3 schematically and diagrammatically depicts a third include of an apparatus according to the disclosure for measuring a property of a transparent tubular object.

FIG. 3 depicts a third include of an apparatus 100c for measuring a property, such as an inner radius or a refractive index, of a transparent tubular object 102, or tube, of which the dimensions are defined by an outer radius $R_D$ and inner radius $R_d$. In FIG. 3, the same reference signs as in FIG. 1 denote the same components, having the same or a similar function.

The apparatus 100c according to FIG. 3 differs from the apparatus 100a according to FIG. 1 in that the laser light originating from the tubular object 102 in the second detection direction at right angles (i.e. at a detection angle α of 90°) to the first detection direction is reflected by a mirror 136 to be in the first detection direction.

It is noted here that the second detection direction can also be selected not to be at right angles to the first detection direction, but at a detection angle α different from 90°, in particular between 45° and 135°, as illustrated in FIG. 2, with the same use and advantages. In such a case, the location and angle of reflection of mirror 136 may be adapted such that the laser light, after reflection on the mirror 136, is parallel to the first detection direction, or in another useful or appropriate direction to pass appropriately positioned second condenser lens 128 to reach appropriately positioned second light detector 132.

Figure 4:
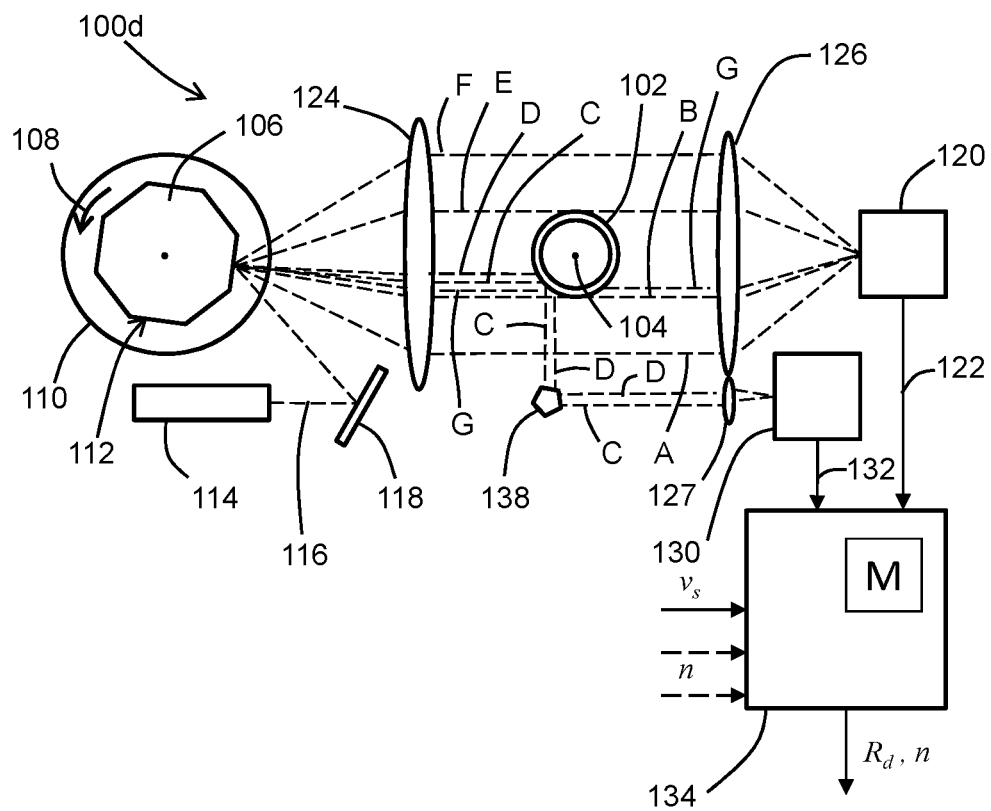
FIG. 4 schematically and diagrammatically depicts a fourth include of an apparatus according to the disclosure for measuring a property of a transparent tubular object.

FIG. 4 depicts a fourth include of an apparatus 100d for measuring a property, such as an inner radius or a refractive index, of a transparent tubular object 102, or tube, of which the dimensions are defined by an outer radius $R_D$ and inner radius $R_d$. In FIG. 4, the same reference signs as in FIG. 3 denote the same components, having the same or a similar function.

The apparatus 100d according to FIG. 4 differs from the apparatus 100c according to FIG. 3 in that the laser light originating from the tubular object 102 in the second detection direction at right angles (i.e. at a detection angle α of 90°) to the first detection direction is reflected by a pentagon prism 138 to be in the first detection direction.

It is noted here that the second detection direction can also be selected not to be at right angles to the first detection direction, but at a detection angle α different from 90°, in particular between 45° and 135°, as illustrated in FIG. 2, with the same use and advantages. Although pentagon prisms are known to conventionally reflect at 90°, in such a case, the location and angle of reflection of pentagon prism 138 may be adapted by adaptation of the orientation of the reflecting and refracting faces of the pentagon prism 138 such that the laser light, after reflection on the pentagon prism 138, is parallel to the first detection direction, or in another useful or appropriate direction to pass appropriately positioned second condenser lens 128 to reach appropriately positioned second light detector 132.

Figure 5:
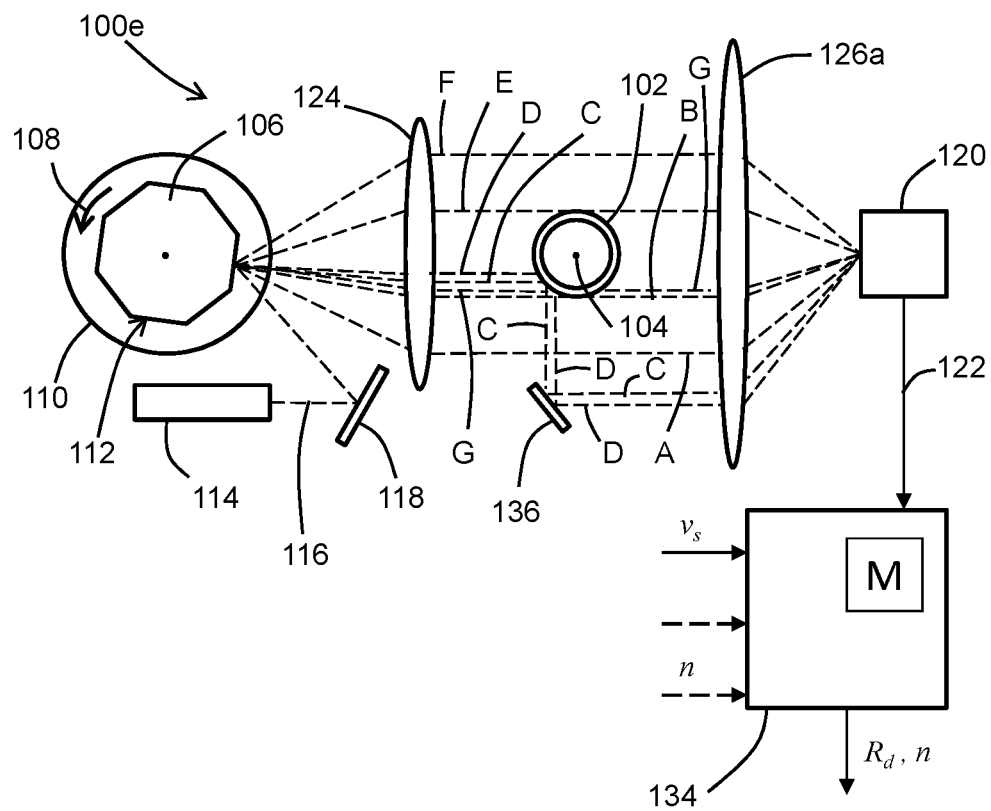
FIG. 5 schematically and diagrammatically depicts a fifth include of an apparatus according to the disclosure for measuring a property of a transparent tubular object.

FIG. 5 depicts a fifth include of an apparatus 100e for measuring a property, such as an inner radius or a refractive index, of a transparent tubular object 102, or tube, of which the dimensions are defined by an outer radius $R_D$ and inner radius $R_d$. In FIG. 5, the same reference signs as in FIG. 1 denote the same components, having the same or a similar function.

The apparatus 100e according to FIG. 5 differs from the apparatus 100a according to FIG. 1 in that the laser light originating from the tubular object 102 in the second detection direction at right angles (i.e. at a detection angle α of 90°) to the first detection direction is reflected by a mirror 136 to be in the first detection direction, and in that the first condenser lens 126a in combination focuses the laser light originating from the tubular object 102 in the first detection direction and in the second detection direction, as reflected by the mirror 136, on the first light detector 120.

In the apparatus 100e, a second light detector 130 can be omitted, and the first light detector 120 is configured to detect laser light according to laser beam positions A, B, C, D, E, F and G. The first output signal 122 from the first light detector 120 is input to the processing system 134.

The detector assembly of the apparatus 100e includes only one light detector.

It is noted here that the second detection direction can also be selected not to be at right angles to the first detection direction, but at a detection angle α different from 90°, in particular between 45° and 135°, as illustrated in FIG. 2, with the same use and advantages. In such a case, the location and angle of reflection of mirror 136 may be adapted or adjustable such that the laser light, after reflection on the mirror 136, is parallel to the first detection direction.

Figure 6:
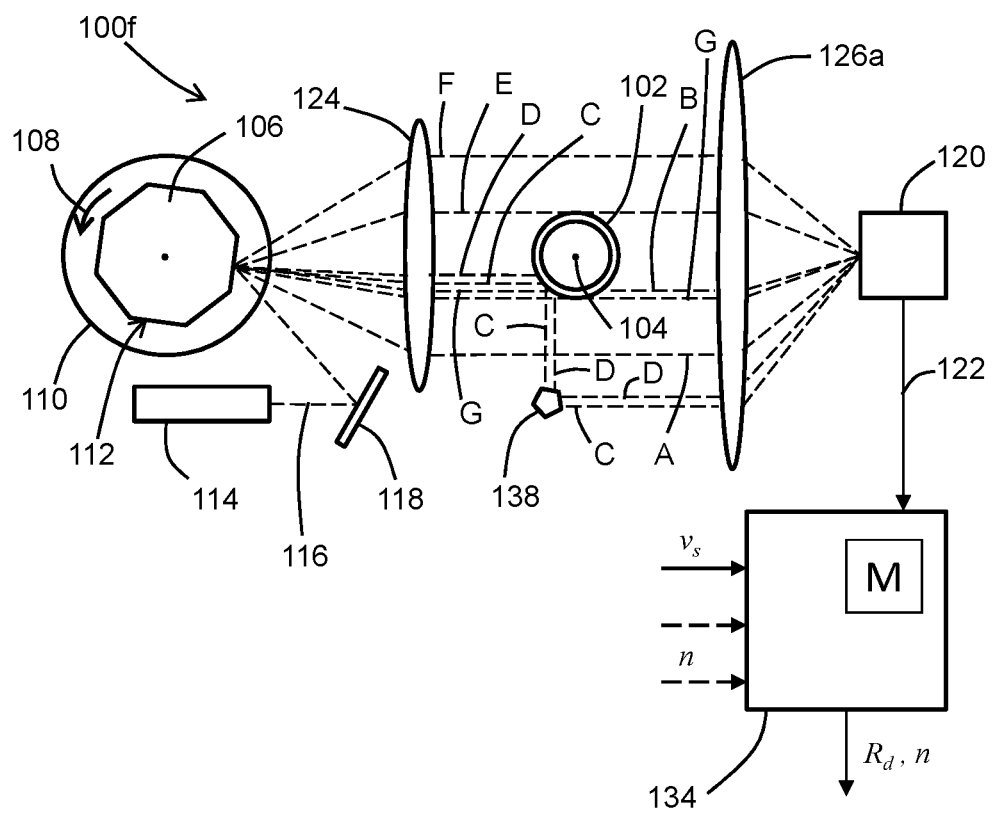
FIG. 6 schematically and diagrammatically depicts a sixth include of an apparatus according to the disclosure for measuring a property of a transparent tubular object.

FIG. 6 depicts a sixth include of an apparatus 100f for measuring a property, such as an inner radius or a refractive index, of a transparent tubular object 102, or tube, of which the dimensions are defined by an outer radius $R_D$ and inner radius $R_d$. In FIG. 6, the same reference signs as in FIG. 5 denote the same components, having the same or a similar function.

The apparatus 100f according to FIG. 6 differs from the apparatus 100e according to FIG. 5 in that the laser light originating from the tubular object 102 in the second detection direction at right angles (i.e. at a detection angle α of 90°) to the first detection direction is reflected by a pentagon prism 138 to be in the first detection direction.

In the apparatus 100f, a second light detector 130 can be omitted, and the first light detector 120 is configured to detect laser light according to laser beam positions A, B, C, D, E, F and G. The first output signal 122 from the first light detector 120 is input to the processing system 134.

The detector assembly of the apparatus 100f includes only one light detector.

It is noted here that the second detection direction can also be selected not to be at right angles to the first detection direction, but at a detection angle α different from 90°, in particular between 45° and 135°, as illustrated in FIG. 2, with the same use and advantages. Although pentagon prisms are known to conventionally reflect at 90°, in such a case, the location and angle of reflection of pentagon prism 138 may be adapted by adaptation of the orientation of the reflecting and refracting faces of the pentagon prism 138 such that the laser light, after reflection on the pentagon prism 138, is parallel to the first detection direction, or in another useful or appropriate direction to pass appropriately positioned second condenser lens 128 to reach appropriately positioned second light detector 132.

Figure 7:
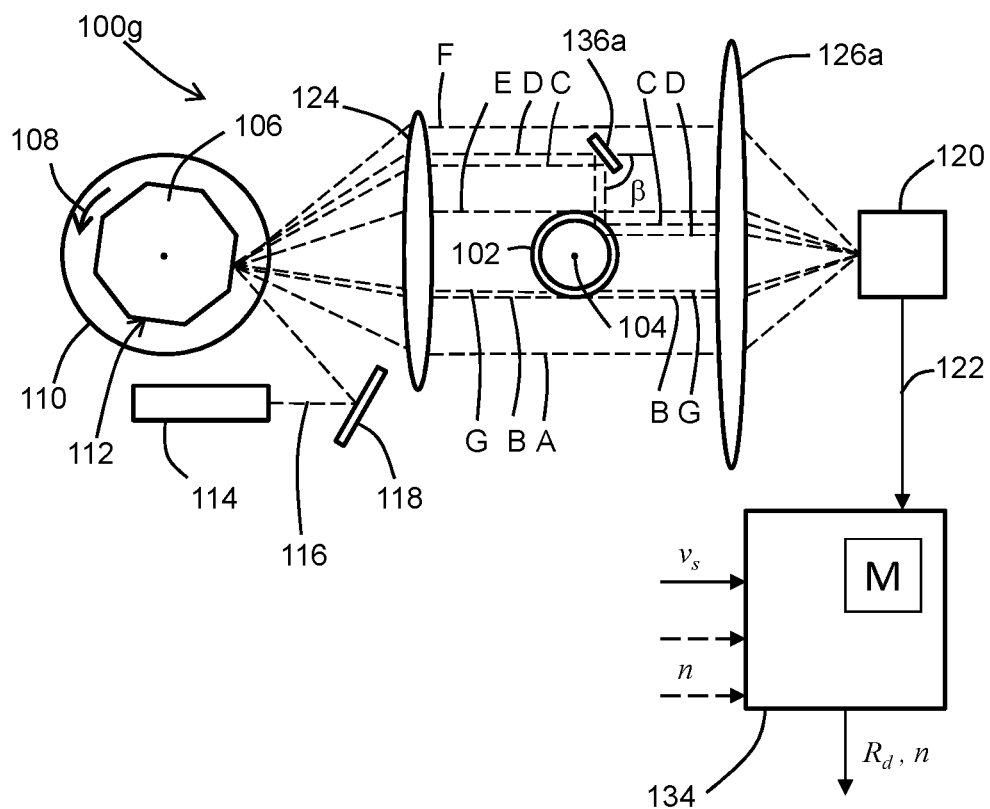
FIG. 7 schematically and diagrammatically depicts a seventh include of an apparatus according to the disclosure for measuring a property of a transparent tubular object.

FIG. 7 depicts a seventh include of an apparatus 100g for measuring a property, such as an inner radius or a refractive index, of a transparent tubular object 102, or tube, of which the dimensions are defined by an outer radius $R_D$ and inner radius $R_d$. In FIG. 7, the same reference signs as in FIG. 5 denote the same components, or components having the same or a similar function.

The apparatus 100g according to FIG. 7 differs from the apparatus 100e according to FIG. 5 in that the scanning laser beam originating from the collimator lens 124 is directed in the first laser beam direction to the tubular object 102 in a first part of the scanning path, and redirected via a mirror 136a in a second laser beam direction to the tubular object at a scanning angle β greater than zero to the first laser beam direction in a second part of the scanning path. In FIG. 7, the first part of the scanning path at least includes laser beams B, G and E, while the second part of the scanning path at least includes laser beams C and D, see also FIG. 12a. In FIG. 7, the scanning angle β is 90°.

The laser light originating from the tubular object 102 in the first detection direction is focused by the first condenser lens 126a on the first light detector 120.

Figure 12A:
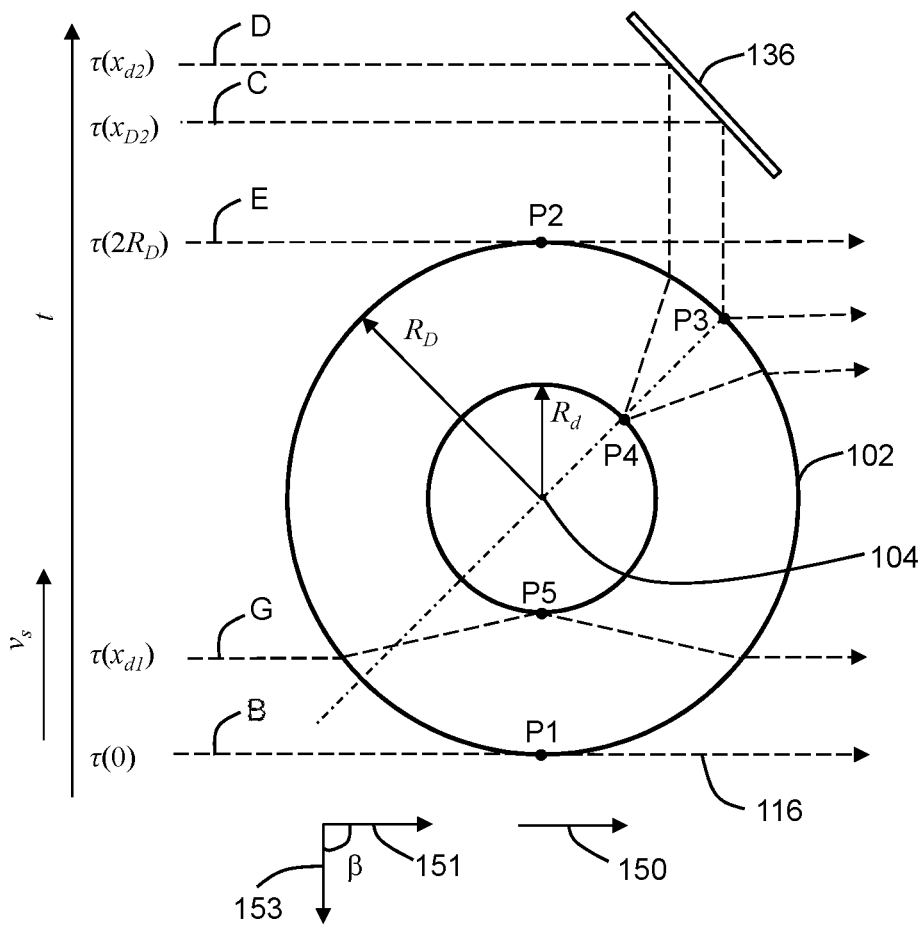
FIGS. 12a and 12b schematically illustrate an alternative scanning, in particular several specific scan positions, of a transparent tubular object.

In the apparatus 100g, a second light detector 130 can be omitted, and the first light detector 120 is configured to detect laser light according to laser beam positions A, B, C, D, E, F and G as seen in FIG. 12a. The first output signal 122 from the first light detector 120 is input to the processing system 134.

The detector assembly of the apparatus 100g includes only one light detector.

It is noted here that the scanning angle β can also be selected to be different from 90°, in particular between 45° and 135°, with the same use and advantages. In such a case, the location and angle of reflection of mirror 136a may be adapted or adjustable such that the laser light, after reflection and refraction by the tubular object 102, is parallel to the first detection direction.

It is noted here that the apparatus 100g may also include a pentagon prism instead of, or in addition to, mirror 136a.

Figure 8:
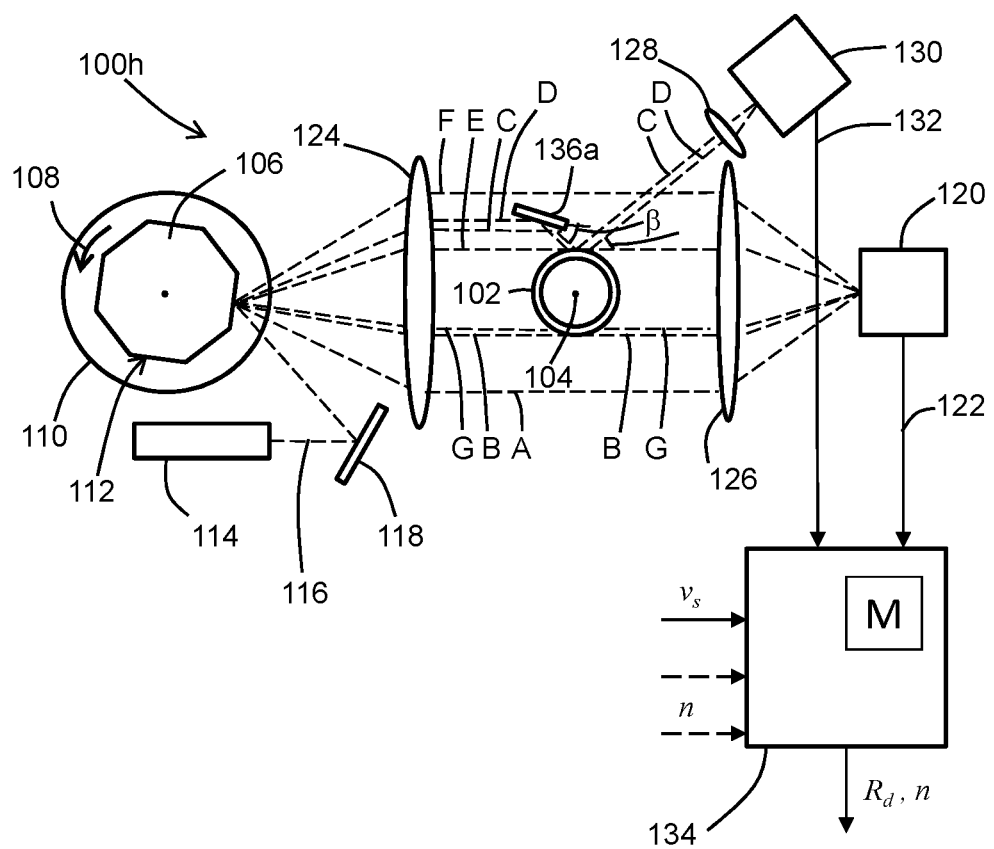
FIG. 8 schematically and diagrammatically depicts an eighth include of an apparatus according to the disclosure for measuring a property of a transparent tubular object.

FIG. 8 depicts an eighth include of an apparatus 100h for measuring a property, such as an inner radius or a refractive index, of a transparent tubular object 102, or tube, of which the dimensions are defined by an outer radius $R_D$ and inner radius $R_d$. In FIG. 8, the same reference signs as in FIG. 7 denote the same components, or components having the same or a similar function.

The apparatus 100h according to FIG. 8 is similar to the apparatus 100g according to FIG. 7 in that the scanning laser beam originating from the collimator lens 124 is directed in the first laser beam direction to the tubular object 102 in a first part of the scanning path, and redirected via a mirror 136a in a second laser beam direction to the tubular object at a scanning angle β greater than zero to the first laser beam direction in a second part of the scanning path. In the apparatus 100h of FIG. 8, like the apparatus 100g of FIG. 7, in the first part of the scanning path at least includes laser beams B, G and E, while the second part of the scanning path at least includes laser beams C and D, as seen in FIG. 12a. In the apparatus 100h of FIG. 8, however, the scanning angle β is smaller than 90°, such as 45°.

The laser light originating from the tubular object 102 in the first detection direction is focused by the first condenser lens 126 on the first light detector 120.

Laser light originating from the tubular object 102 in a second detection direction at a detection angle α is focused by second condenser lens 128 on second light detector 130. Such an arrangement is particularly useful when often tubular objects 102 with substantially the same outer radius RD and substantially the same inner radius Rd are measured. The sum of the detection angle and the scanning angle (α+β) can be selected, in particular between 45° and 135°, to have an optimum sensitivity for the inner radius Rd. Accordingly, the second condenser lens 128 and the second light detector 130 take an appropriately adjusted position with respect to the tubular object 102.

It is noted here that the apparatus 100h may also include a pentagon prism instead of, or in addition to, mirror 136a.

Figure 9:
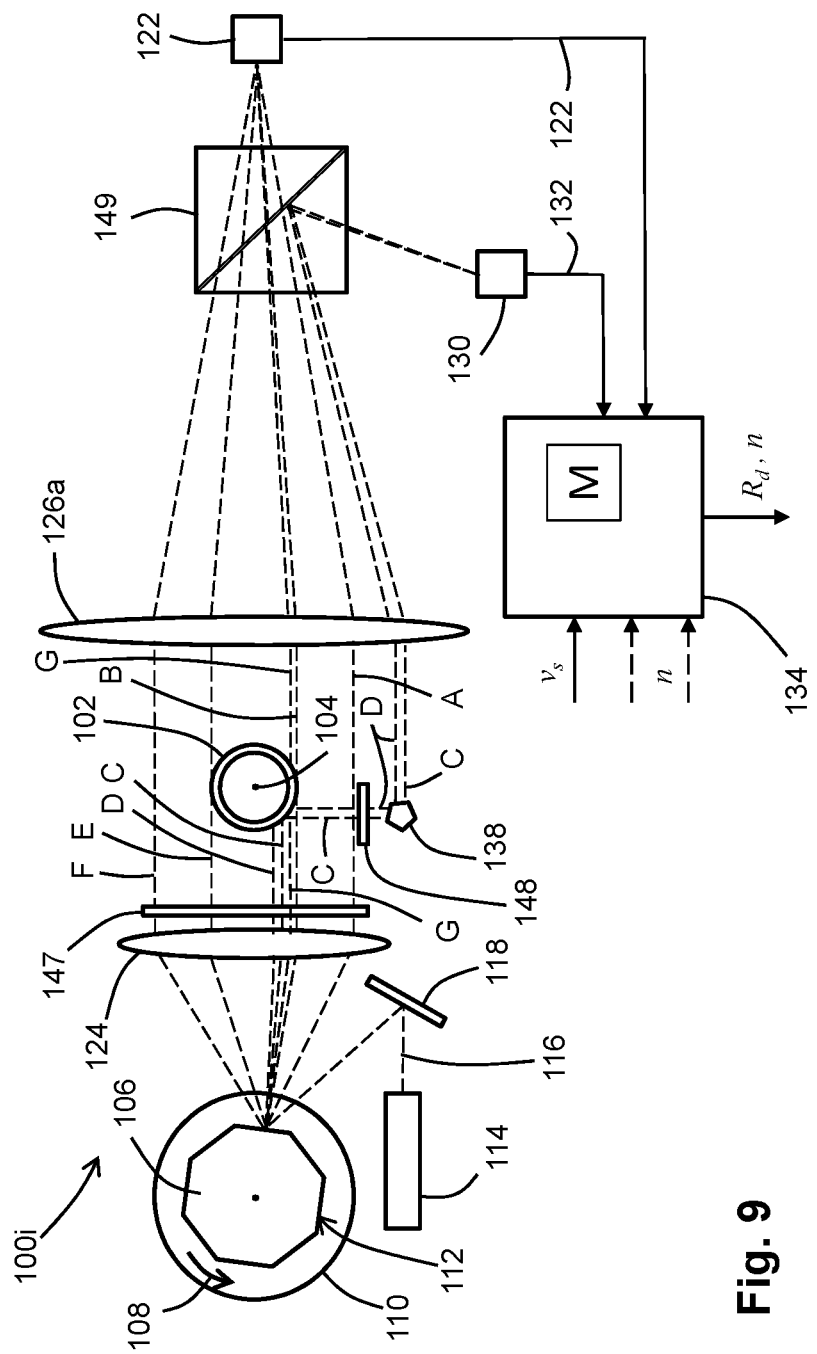
FIG. 9 schematically and diagrammatically depicts an ninth include of an apparatus according to the disclosure for measuring a property of a transparent tubular object.

FIG. 9 depicts a ninth include of an apparatus 100i for measuring a property, such as an inner radius or a refractive index, of a transparent tubular object 102, or tube, of which the dimensions are defined by an outer radius $R_D$ and inner radius $R_d$. In FIG. 9, the same reference signs as in FIG. 6 denote the same components, having the same or a similar function.

The apparatus 100i according to FIG. 9 differs from the apparatus 100f according to FIG. 6 in the following aspects. A laser beam polarizer 147 is arranged in the path of the scanning laser beam 116 between the laser beam scanner, including the laser beam generator 114, the rotatable mirror assembly 106 and the collimator lens 124, and the (envisaged location of the) tubular object 102. A waveplate 148, such as a half-lambda plate, is arranged in the path of the laser light originating from the tubular object 102 in the first detection direction, between the (envisaged location of the) tubular object 102 and the pentagon prism 138. A polarizing beamsplitter 149 is arranged in the path of the laser light originating from the first condenser lens 126a, between the first condenser lens 126a and the first light detector 120.

It is noted here that the apparatus 100i may also include a mirror 136 instead of, or in addition to, pentagon prism 138.

The laser beam polarizer 147 and the waveplate 148 have the effect that the first laser light originating from the tubular object 102 in the first detection direction has a polarization that is different from the polarization of the second laser light originating from the tubular object 102 in the second detection direction. In the polarizing beamsplitter 149, the first laser light is split off the second laser light, and directed to the first light detector 120. The second laser light is split off the first laser light, and directed to the second light detector 130.

Figure 10:
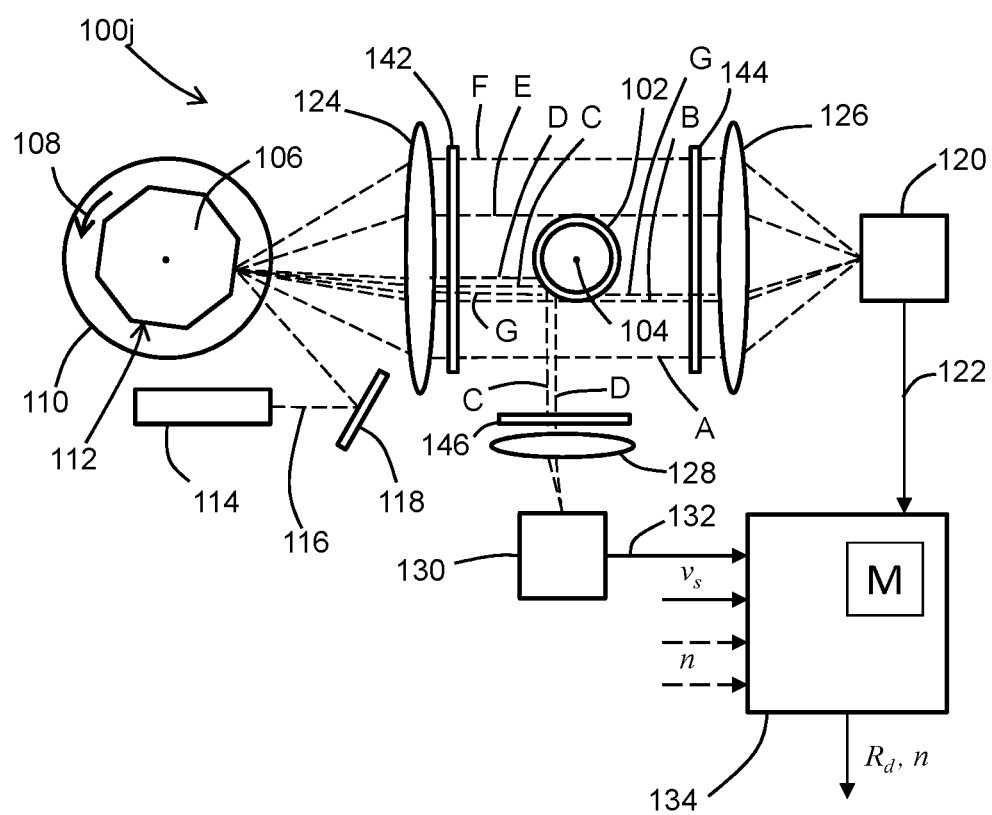
FIG. 10 schematically and diagrammatically depicts an tenth include of an apparatus according to the disclosure for measuring a property of a transparent tubular object.

FIG. 10 depicts an eighth include of an apparatus 100j for measuring a property, such as an inner radius or a refractive index, of a transparent tubular object 102, or tube, of which the dimensions are defined by an outer radius $R_D$ and inner radius $R_d$. In FIG. 10, the same reference signs as in FIGS. 1 to 9 denote the same components, having the same or a similar function.

The apparatus 100j according to FIG. 10 differs from the apparatus 100a according to FIG. 1 in the following aspects. A first polarizer 142 having a 45° polarizing direction is arranged in the path of the scanning laser beam 116 between the laser beam scanner, including the laser beam generator 114, the rotatable mirror assembly 106 and the collimator lens 124, and the (envisaged location of the) tubular object 102. A second polarizer 144 having a (−45+δ)° (wherein |ε|>0) polarizing direction is arranged in the path of the laser light originating from the tubular object 102 in the first detection direction between the (envisaged location of the) tubular object 102 and the first condenser lens 126. A third polarizer 146 having a (45+ε)° (wherein |ε|>0) polarizing direction is arranged in the path of the laser light originating from the tubular object 102 in the second detection direction between the (envisaged location of the) tubular object 102 and the second condenser lens 128.

As the reflection and refraction of the laser beams are polarization-dependent, the mutual signal strengths can be optimized using polarizers at the laser beam and/or at the first and second light detectors 120, 130.

The first polarizer 142 is arranged in the laser beam after it has passed the collimator lens 124. The polarizing direction of the first polarizer 142 is 45° relative to longitudinal axis 104 of the tubular object 102. The second polarizer 144 is arranged before the condenser lens 126, 126a having a polarizing direction of −45°+δ relative to the longitudinal axis 104 of the tubular object 102. When the angle is exactly −45°, i.e. δ=0, the laser light outside of the tubular object will be basically extinct, i.e. will not arrive at the first light detector 120. However, the laser light passing through the tube will be mainly p-polarized and pass the second polarizer 144. By rotating the second polarizer 144 over an angle δ, the intensities of the fully transmitted laser beam outside the tube, and the laser light that is transmitted inside the tube, can be balanced. For the laser light in the second detection direction, the third polarizer 146 can be put at a polarizing direction of nominally 45°. By varying this angle over an angle ε, the light intensities of the directly reflected beam (laser light beam C), and the laser light that is reflected at the inner radius of the tubular object 102 (laser light beam D), can be balanced.

It is noted that the includes of apparatus 100b (FIG. 2), apparatus 100c (FIG. 3), apparatus 100d (FIG. 4), apparatus 100e (FIG. 5), apparatus 100f (FIG. 6), apparatus 100g (FIG. 7), apparatus 100h (FIG. 8) and other includes each can also be equipped with first, second and third polarizers 142, 144, 146. In the include of apparatus 100b, third polarizer 146 may be arranged in the path of the laser light originating from the tubular object 102 in the second detection direction between the (envisaged location of the) tubular object 102 and the second condenser lens 128a. In the includes of apparatus 100c and apparatus 100e, third polarizer 146 may be arranged in the path of the laser light originating from the tubular object 102 in the second detection direction between the (envisaged location of the) tubular object 102 and the mirror 136. In the includes of apparatus 100d and apparatus 100f, third polarizer 146 may be arranged in the path of the laser light originating from the tubular object 102 in the second detection direction between the (envisaged location of the) tubular object 102 and the pentagon prism 138. In the includes of apparatus 100g and apparatus 100h, third polarizer 146 may be arranged in the path of the laser light originating from the mirror 136a between the mirror 136a and the (envisaged location of the) tubular object 102. In the include of apparatus 100h, third polarizer 146 may alternatively be arranged in the path of the laser light originating from the tubular object 102 between the (envisaged location of the) tubular object 102 and the second condenser lens 128.

In the includes shown in FIGS. 1 to 10, a scanning laser beam is generated by the laser beam generator 114 interacting (through reflecting mirror 118, or directly) with the rotating mirror assembly 106 and the collimator lens 124. However, other devices producing the scanning laser beam can be applied as well. Thus, the combination of the laser beam generator 114, the rotating mirror assembly 106 and the collimator lens 124 is not essential to the present disclosure.

Figure 11A:
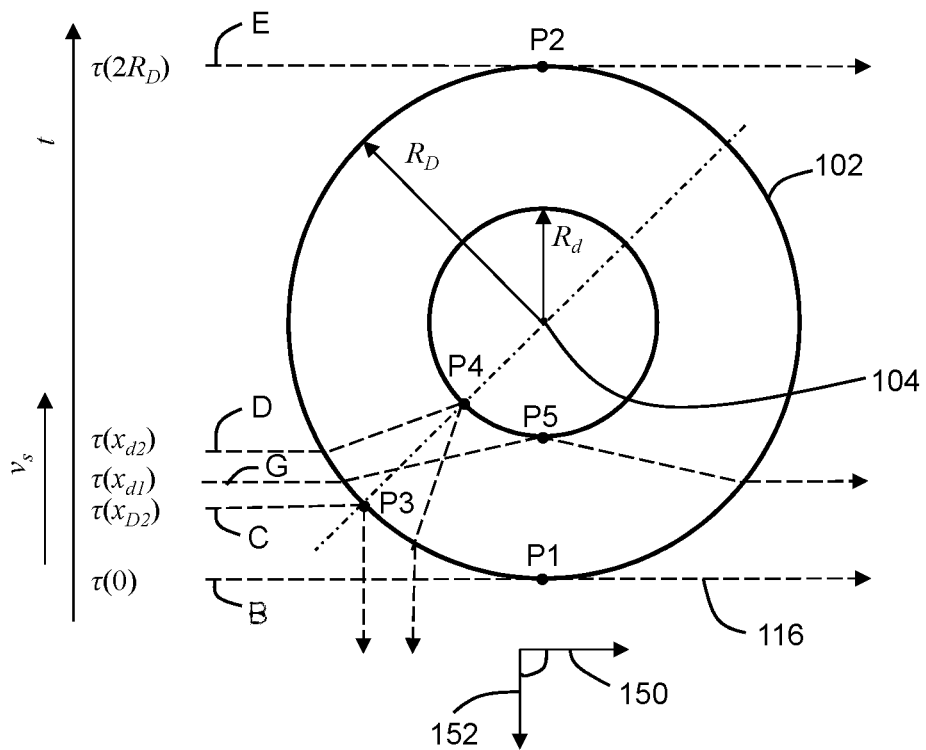
FIGS. 11a and 11b schematically illustrate a scanning, in particular several specific scan positions, of a transparent tubular object.

FIG. 11a illustrates a scanning of a tubular object 102 by a laser beam being moved along a scanning path in a scanning direction at right angles to the longitudinal axis 104 of the tubular object 102 and at right angles to the laser beam direction with a constant speed $v_s$. For clarity of explanation, the tubular object 102 is shown with a great thickness, however, in practice a difference between the outer radius, $R_D$, and the inner radius, $R_d$, of the tubular object 102 may be quite small.

Figure 11B:
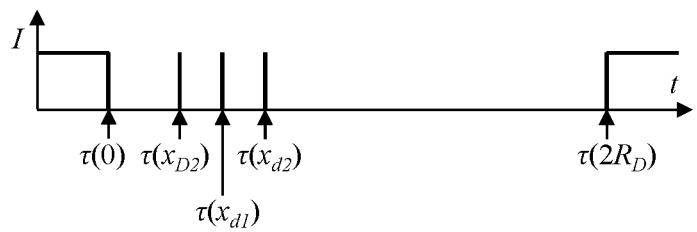

With the first light detector 120 and, depending on the particular include as explained before, possibly also the second light detector 130, according to apparatus 100a, 100b, 100c, 100d, 100e, 100f, 100i or 100j, or variations thereof using the same principles, the intensity of the laser light is measured. FIG. 11b illustrates the intensity I of the laser light as detected by the first light detector 120 and possibly also the second light detector 130, at different times t. It is noted here that the indications of laser light intensity I should be understood as high and low, respectively, where it not intended to show an absolute value, and where intensity transitions may be more gradual in time.

The following events take place that affect the output signal of the light detector 120 and light detector 130, if present:

At laser beam position B, the laser beam in the first laser beam direction strikes the outer edge of the tubular object 102. Here, the laser beam is tangential to the outer surface of the tubular object 102 at the first point P1 of the tubular object 102 at a first time, $\tau(0)$, detectable in the intensity of the laser light in the first detection direction, as indicated by arrow 150, the first detection direction directed parallel to the original laser beam direction.

At laser beam position C, the laser beam is reflected at the outer surface of the tubular object 102 at the third point P3 of the tubular object 102 at a third time, $\tau(x_{D2})$, detectable in the intensity of the laser light in the second detection direction, as indicated by arrow 152, at a detection angle α of 90° (as shown in FIG. 9) to, or at a detection angle α between 45° and 135° to the first detection direction.

At laser beam position D, the laser beam is refracted at the outer surface of the tubular object 102, is reflected at the inner surface of the tubular object 102 at the fourth point P4 of the tubular object 102, and is refracted again at the outer surface of the tubular object 102 at a fourth time, $\tau(x_{d2})$, detectable in the intensity of the laser light in the second detection direction.

At laser beam position E, the laser beam strikes the outer edge of the tubular object 102. Here, the laser beam is tangential to the outer surface of the tubular object 102 at the second point P2 of the tubular object 102 at a second time, $\tau(2R_D)$, detectable in the intensity of the laser light in the first detection direction.

At laser beam position G, the laser beam is refracted at the outer surface of the tubular object 102, is reflected at the inner surface of the tubular object 102 at the fifth point P5 of the tubular object 102, and is refracted again at the outer surface of the tubular object 102 at a fifth time, $\tau(x_{d1})$, detectable in the intensity of the laser light in the first detection direction.

FIG. 12a illustrates a scanning of a tubular object 102 by a laser beam being moved along a scanning path in a scanning direction at right angles to the longitudinal axis 104 of the tubular object 102 and at right angles to the laser beam direction with a constant speed $v_s$. For clarity of explanation, the tubular object 102 is shown with a great thickness, however, in practice a difference between the outer radius, $R_D$, and the inner radius, $R_d$, of the tubular object 102 may be quite small.

Figure 12B:
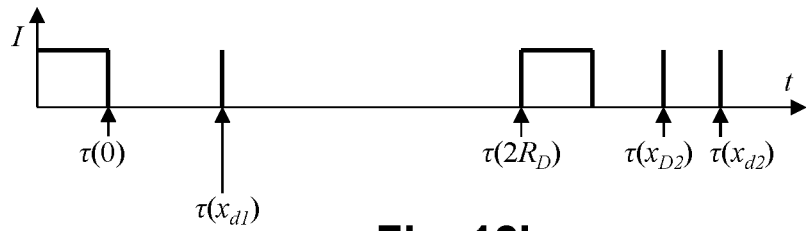

With the first light detector 120 and, depending on the particular include as explained before, possibly also the second light detector 130, with the apparatus 100g or 100h, or variations thereof using the same principles, the intensity of the laser light is measured. FIG. 12b illustrates the intensity I of the laser light as detected by the first light detector 120 and possibly also the second light detector 130, at different times t. It is noted here that the indications of laser light intensity I should be understood as high and low, respectively, where it not intended to show an absolute value, and where intensity transitions may be more gradual in time.

The following events take place that affect the output signal of the light detector 120 and light detector 130, if present:

At laser beam position B, the laser beam in the first laser beam direction 151 strikes the outer edge of the tubular object 102. Here, the laser beam is tangential to the outer surface of the tubular object 102 at the first point P1 of the tubular object 102 at a first time, $\tau(0)$, detectable in the intensity of the laser light in the first detection direction, as indicated by arrow 150, the first detection direction directed parallel to the original laser beam direction.

At laser beam position G, the laser beam is refracted at the outer surface of the tubular object 102, is reflected at the inner surface of the tubular object 102 at the fifth point P5 of the tubular object 102, and is refracted again at the outer surface of the tubular object 102 at a fifth time, $\tau(x_{d1})$, detectable in the intensity of the laser light in the first detection direction, as indicated by arrow 150.

At laser beam position E, the laser beam strikes the outer edge of the tubular object 102. Here, the laser beam is tangential to the outer surface of the tubular object 102 at the second point P2 of the tubular object 102 at a second time, $\tau(2R_D)$, detectable in the intensity of the laser light in the first detection direction, as indicated by arrow 150.

At laser beam position C, the laser beam is reflected by mirror 136 to tubular object 102 to be directed in the second laser beam direction 151 at a scanning angle β (in FIG. 12a: 90°) to the first laser beam direction, and is reflected at the outer surface of the tubular object 102 at the third point P3 of the tubular object 102 at a third time, $\tau(x_{D2})$, detectable in the intensity of the laser light in the first detection direction, as indicated by arrow 150, at a detection angle α of 0° (as shown in FIG. 7) to, or at a detection angle α such that the sum (α+β) is between 45° and 135° (as shown in FIG. 8).

At laser beam position D, the laser beam is refracted at the outer surface of the tubular object 102, is reflected at the inner surface of the tubular object 102 at the fourth point P4 of the tubular object 102, and is refracted again at the outer surface of the tubular object 102 at a fourth time, $\tau(x_{d2})$, detectable in the intensity of the laser light.

In FIG. 11b, it is seen that the time $\tau(x_{d1})$ is between, or at least close to, $\tau(x_{D2})$ and $\tau(x_{d2})$ which, when measuring tubular objects 102 having certain dimensions, may lead to difficulties of detecting any of the associated light intensities $\tau(x_{D2})$, $\tau(x_{d1})$ or $\tau(x_{d2})$, since the peaks of the light intensities may follow each other closely in time. In FIG. 12b, it is seen that such difficulties are reduced, since the times τ($x_{D2}$) and τ($x_{d2}$) have been separated in time from time τ($x_{d1}$), and thus each of these three times are more clearly detectable.

The outer tube diameter D is related to the scanning speed $v_s$ by $$D = 2R_D = v_s \cdot (\tau(2R_D) - \tau(0))$$

This scanning speed $v_s$ is assumed constant. By way of example, the scanning speed $v_s$ may be determined by calibration of the apparatus 100a, 100b, 100c, 100d, 100e, 100f, 100g, 100h, 100i and 100j by measuring the first time, τ(0), and the second time, τ(2$R_D$), from a reference cylindrical object 102 with a known (calibrated) diameter.

Using the theory developed in the Jablonski et al. reference, and correcting an error presented therein, the inner tube radius, $R_d$, may be calculated by the processing system 134 in the apparatus 100a, 100b, 100c, 100d, 100e, 100f, 100i or 100j, or similar apparatus, based on the determination of the first, second, third and fourth times, and the equation:

$$R_d = R_D \cdot \frac{1 - \frac{x_{d2}}{R_D}}{n \cdot \sin\left(\frac{\alpha}{2} + \arcsin\left(\frac{1 - \frac{x_{d2}}{R_D}}{n}\right) - \arcsin\left(1 - \frac{x_{d2}}{R_D}\right)\right)},$$

wherein:

$$R_D = \frac{v_s}{2} \cdot (\tau(2R_D) - \tau(0))$$

and $$x_{d2} = R_D \cdot \left(\frac{2(\tau(x_{d2}) - \tau(x_{D2}))}{\tau(2R_D) - \tau(0)} + 1 - \sin(\alpha/2)\right).$$

In the latter relationship, $x_{d2}$ denotes laser beam position D as it is detected in the second detection direction, wherein laser beam position D is measured relative to laser beam position B being a zero position.

Using the theory developed in the Jablonski et al. reference, and correcting an error presented therein, the inner tube radius, $R_d$, may be calculated by the processing system 134 in the apparatus 100g or 100h based on the determination of the first, second, third and fourth times, and the equation:

$$R_d = R_D \cdot \frac{1 - \frac{x_{d2}}{R_D}}{n \cdot \sin\left(\frac{\alpha + \beta}{2} + \arcsin\left(\frac{1 - \frac{x_{d2}}{R_D}}{n}\right) - \arcsin\left(1 - \frac{x_{d2}}{R_D}\right)\right)},$$

wherein:

$$R_D = \frac{v_s}{2} \cdot (\tau(2R_D) - \tau(0))$$

and $$x_{d2} = R_D \cdot \left(\frac{2(\tau(x_{d2}) - \tau(x_{D2}))}{\tau(2R_D) - \tau(0)} + 1 - \sin((\alpha + \beta)/2)\right).$$

In the latter relationship, $x_{d2}$ denotes laser beam position D as it is detected in the first or second detection direction, wherein laser beam position D is measured relative to laser beam position B being a zero position.

Figure 13:
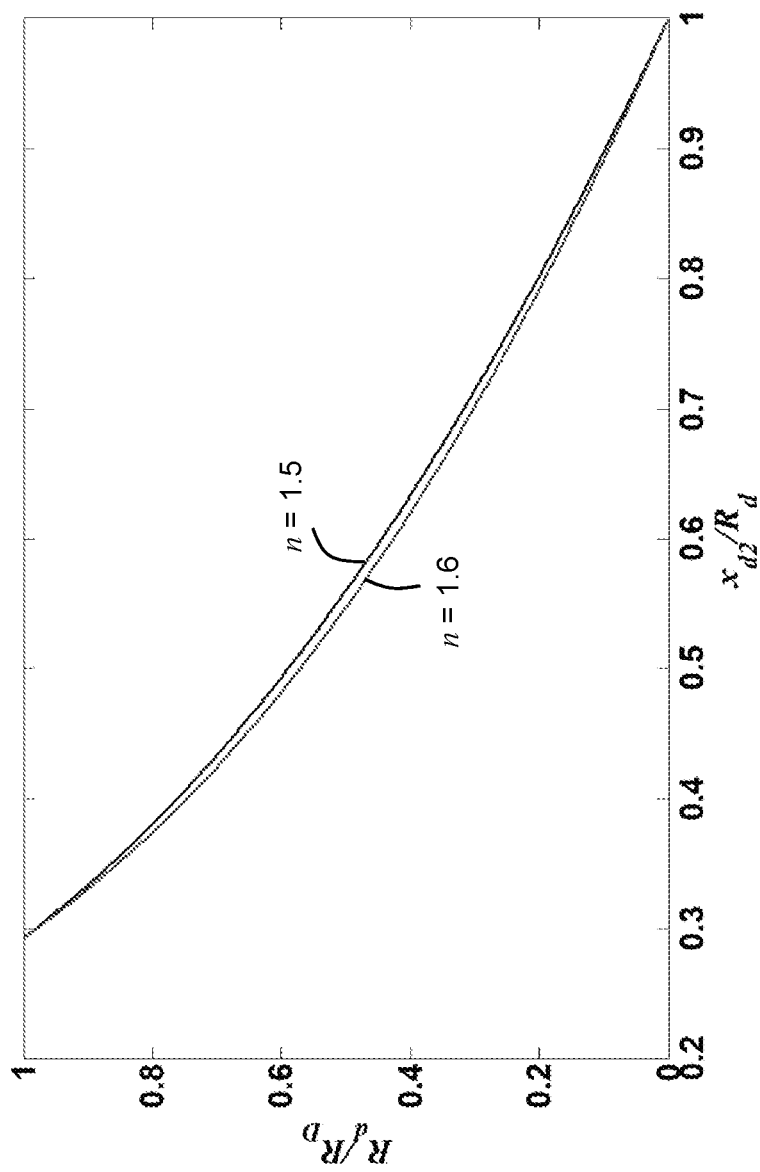
FIG. 13 shows graphs showing the relationship between relative signal timing and relative inner tube diameter for two refractive indexes of the material of the tubular object.

FIG. 13 gives the relationship between the relative signal timing and the relative inner tube diameter for two refractive indexes. The relationship remains rather linear in most areas, also for thinner tubes. This means that also thin tubes can be measured in this way with reasonable uncertainty.

When the inner tube surface is well measurable in the first laser beam direction, the first detection direction and in the second detection direction, the refractive index n can be eliminated from the equations based on measuring the fifth time, τ($x_{d1}$), and an absolute measurement of $R_d$ can be obtained in the apparatus 100a, 100b, 100c, 100d, 100e, 100f, 100i or 100j, or similar apparatus, without prior knowledge of n, based on measuring the first, second, third, fourth and fifth times, and the equation:

$$R_d = R_D \frac{1}{b + \sqrt{b^2 - 1}}$$

wherein:

$$R_D = \frac{v_s}{2} \cdot (\tau(2R_D) - \tau(0)),$$

$$b = \frac{g \sin\beta_1 - \cos\left(\frac{\alpha}{2} - \beta_2\right)}{g - 1},$$

$$g = \left(\tan\beta_1 \frac{\sin\left(\frac{\alpha}{2} - \beta_2\right)}{\sin\beta_2}\right)^2,$$

$$\beta_1 = \arcsin\left(1 - \frac{x_{d1}}{R_D}\right),$$

$$\beta_2 = \arcsin\left(1 - \frac{x_{d2}}{R_D}\right),$$

$$x_{d1} = v_s \cdot (\tau(x_{d1}) - \tau(0)) = 2 \cdot R_d \cdot \frac{(\tau(x_{d1}) - \tau(0))}{(\tau(2R_D) - \tau(0))},$$

and $$x_{d2} = R_D \cdot \left(\frac{2(\tau(x_{d2}) - \tau(x_{D2}))}{\tau(2R_D) - \tau(0)} + 1 - \sin(\alpha/2)\right).$$

As an additional result, as indicated in FIGS. 1 to 6, 9 and 10, the processing system 134 may produce the refractive index n based on the equation:

$$n = \sin\beta_1 \sqrt{\left(\frac{\left(\frac{R_D}{R_d}\right) - \sin\beta_1}{\cos\beta_1}\right)^2 + 1}$$

or the equation $$n = \sin\beta_2 \sqrt{\left(\frac{\left(\frac{R_D}{R_d}\right) - \cos\left(\frac{\alpha}{2} - \beta_2\right)}{\sin\left(\frac{\alpha}{2} - \beta_2\right)}\right)^2 + 1}.$$

When the inner tube surface is well measurable in the first laser beam direction, the second laser beam direction, the first detection direction and in the second detection direction, the refractive index n can be eliminated from the equations based on measuring the fifth time, $\tau(x_{d1})$, and an absolute measurement of $R_d$ can be obtained in the apparatus 100g or 100h, or similar apparatus, without prior knowledge of n, based on measuring the first, second, third, fourth and fifth times, and the equation:

$$R_d = R_D \frac{1}{b + \sqrt{b^2 - 1}}$$

wherein:

$$R_D = \frac{v_s}{2} \cdot (\tau(2R_D) - \tau(0)),$$

$$b = \frac{g\sin\beta_1 - \cos\left(\frac{\alpha+\beta}{2} - \beta_2\right)}{g - 1},$$

$$g = \left(\tan\beta_1 \frac{\sin\left(\frac{\alpha+\beta}{2} - \beta_2\right)}{\sin\beta_2}\right)^2,$$

$$\beta_1 = \arcsin\left(1 - \frac{x_{d1}}{R_D}\right),$$

$$\beta_2 = \arcsin\left(1 - \frac{x_{d2}}{R_D}\right),$$

$$x_{d1} = v_s \cdot (\tau(x_{d1}) - \tau(0)) = 2 \cdot R_d \cdot \frac{(\tau(x_{d1}) - \tau(0))}{(\tau(2R_D) - \tau(0))},$$

and $$x_{d2} = R_D \cdot \left(\frac{2(\tau(x_{d2}) - \tau(x_{D2}))}{\tau(2R_D) - \tau(0)} + 1 - \sin((\alpha+\beta)/2)\right).$$

As an additional result, as indicated in FIGS. 7 and 8, the processing system 134 may produce the refractive index n based on the equation:

$$n = \sin\beta_1 \sqrt{\left(\frac{\left(\frac{R_D}{R_d}\right) - \sin\beta_1}{\cos\beta_1}\right)^2 + 1}$$

or the equation $$n = \sin\beta_2 \sqrt{\left(\frac{\left(\frac{R_D}{R_d}\right) - \cos\left(\frac{\alpha+\beta}{2} - \beta_2\right)}{\sin\left(\frac{\alpha+\beta}{2} - \beta_2\right)}\right)^2 + 1}.$$

Hence, this disclosure also relates to a method for measuring a property of a transparent tubular object having a longitudinal axis, the method including:

scanning a laser beam in a scanning direction with a constant scanning speed, $v_s$, along a scanning path at right angles to the longitudinal axis of the object, wherein the scanning laser beam is directed in a first laser beam direction to the object at right angles to the scanning direction and at right angles to the longitudinal axis of the object;

detecting an intensity of laser light originating from the object in a first detection direction parallel to the laser beam direction;

determining a first time, $\tau(0)$, and a second time, $\tau(2R_D)$, from the intensity of the laser light detected in the first detection direction, $\tau(0)$ being representative of the laser beam being tangential to the outer surface of the object at a first point of the object, and $\tau(2R_D)$ being representative of the laser beam being tangential to the outer surface of the object at a second point of the object diametrically opposite the first point;

detecting an intensity of laser light originating from the object in a second detection direction at a detection angle, a, greater than zero to the first detection direction;

determining a third time, $\tau(x_{D2})$, and a fourth time, $\tau(x_{d2})$, from the intensity of the laser light detected in the second detection direction, $\tau(x_{D2})$ being representative of the laser beam being reflected at the outer surface of the object at a third point of the object, and $\tau(x_{d2})$ being representative of the laser beam being refracted at the outer surface of the object and reflected at the inner surface of the object at a fourth point of the object; and determining a fifth time, $\tau(x_{d1})$, from the intensity of the laser light detected in the first detection direction, $\tau(x_{d1})$ being representative of the laser beam being refracted at the outer surface of the object and reflected at the inner surface of the object at a fifth point of the object; and calculating a refractive index, n, of the object based on $v_s$, a, $\tau(0)$, $\tau(2R_D)$, $\tau(x_{D2})$, $\tau(x_{d2})$ and $\tau(x_{d1})$, wherein calculating n includes calculating a difference between $\tau(2R_D)$ and $\tau(0)$, and a difference between $\tau(x_{d2})$ and $\tau(x_{D2})$.

Also, the present disclosure is related to a method for measuring a property of a transparent tubular object having a longitudinal axis, the method including:

scanning a laser beam in a scanning direction with a constant scanning speed, $v_s$, along a scanning path at right angles to the longitudinal axis of the object, wherein the laser beam is directed at right angles to the longitudinal axis of the object, wherein the scanning laser beam is directed in a first laser beam direction to the object at right angles to the scanning direction in a first part of the scanning path, and redirected via a reflector in a second laser beam direction to the object at a scanning angle, β, greater than zero to the first laser beam direction in a second part of the scanning path;

detecting an intensity of laser light originating from the object in a first detection direction parallel to the laser beam direction;

determining a first time, $\tau(0)$, and a second time, $\tau(2R_D)$, from the intensity of the laser light detected in the first detection direction, $\tau(0)$ being representative of the laser beam being tangential to the outer surface of the object at a first point of the object, and $\tau(2R_D)$ being representative of the laser beam being tangential to the outer surface of the object at a second point of the object diametrically opposite the first point;

detecting an intensity of laser light originating from the object in a second detection direction at a detection angle, a, to the first detection direction;

determining a third time, $\tau(x_{D2})$, and a fourth time, $\tau(x_{d2})$, from the intensity of the laser light detected in the second detection direction, $\tau(x_{D2})$ being representative of the laser beam being reflected at the outer surface of the object at a third point of the object, and $\tau(x_{d2})$ being representative of the laser beam being refracted at the outer surface of the object and reflected at the inner surface of the object at a fourth point of the object;

determining a fifth time, $\tau(x_{d1})$, from the intensity of the laser light detected in the first detection direction, $\tau(x_{d1})$ being representative of the laser beam being refracted at the outer surface of the object and reflected at the inner surface of the object at a fifth point of the object; and calculating a refractive index, n, of the object based on $v_s$, α, β, τ(0), τ($2R_D$), τ($x_{D2}$), τ($x_{d2}$) and τ($x_{d1}$), wherein calculating n includes calculating a difference between τ($2R_D$) and τ(0), and a difference between τ($x_{d2}$) and τ($x_{D2}$).

Also, the present disclosure is related to an apparatus for measuring a property of a transparent tubular object having a longitudinal axis, the apparatus including:

a laser beam scanner configured for scanning a laser beam in a scanning direction with a constant scanning speed, $v_s$, along a scanning path at right angles to the longitudinal axis of the object, wherein the scanning laser beam is directed in a first laser beam direction to the object at right angles to the scanning direction and at right angles to the longitudinal axis of the object;

a detector assembly configured for detecting an intensity of laser light originating from the object in a first detection direction parallel to the first laser beam direction, and detecting an intensity of laser light originating from the object in a second detection direction at a detection angle, a, greater than zero to the first detection direction; and a processing system configured for:

determining a first time, τ(0), and a second time, τ($2R_D$), from the intensity of the laser light detected in the first detection direction, τ(0) being representative of the laser beam being tangential to the outer surface of the object at a first point of the object, and τ($2R_D$) being representative of the laser beam being tangential to the outer surface of the object at a second point of the object diametrically opposite the first point;

determining a third time, τ($x_{D2}$), and a fourth time, τ($x_{d2}$), from the intensity of the laser light detected in the second detection direction, τ($x_{D2}$) being representative of the laser beam being reflected at the outer surface of the object at a third point of the object, and τ($x_{d2}$) being representative of the laser beam being refracted at the outer surface of the object and reflected at the inner surface of the object at a fourth point of the object;

determining a fifth time, τ($x_{d1}$), from the intensity of the laser light detected in the first detection direction, τ($x_d$j) being representative of the laser beam being refracted at the outer surface of the object and reflected at the inner surface of the object at a fifth point of the object; and calculating a refractive index, n, of the object based on $v_s$, a, τ(0), τ($2R_D$), τ($x_{D2}$), τ($x_{d2}$) and τ($x_{d1}$), wherein calculating n includes calculating a difference between τ($2R_D$) and τ(0), and a difference between τ($x_{d2}$) and τ($x_{D2}$).

Also the present disclosure is related to an apparatus for measuring a property of a transparent tubular object having a longitudinal axis, the apparatus including:

a laser beam scanner configured for scanning a laser beam in a scanning direction with a constant scanning speed, $v_s$, along a scanning path at right angles to the longitudinal axis of the object, wherein the laser beam is directed at right angles to the longitudinal axis of the object, wherein the scanning laser beam is directed in a first laser beam direction to the object at right angles to the scanning direction in a first part of the scanning path, and redirected via a reflector in a second laser beam direction to the object at a scanning angle, β, greater than zero to the first laser beam direction in a second part of the scanning path;

a detector assembly configured for detecting an intensity of laser light originating from the object in a first detection direction parallel to the laser beam direction, and detecting an intensity of laser light originating from the object in a second detection direction at a detection angle, a, to the first detection direction; and a processing system configured for:

determining a first time, τ(0), and a second time, τ($2R_D$), from the intensity of the laser light detected in the first detection direction, τ(0) being representative of the laser beam being tangential to the outer surface of the object at a first point of the object, and τ($2R_D$) being representative of the laser beam being tangential to the outer surface of the object at a second point of the object diametrically opposite the first point;

determining a third time, τ($x_{D2}$), and a fourth time, τ($x_{d2}$), from the intensity of the laser light detected in the second detection direction, τ($x_{D2}$) being representative of the laser beam being reflected at the outer surface of the object at a third point of the object, and τ($x_{d2}$) being representative of the laser beam being refracted at the outer surface of the object and reflected at the inner surface of the object at a fourth point of the object;

determining a fifth time, τ($x_{d1}$), from the intensity of the laser light detected in the first detection direction, τ($x_{d1}$) being representative of the laser beam being refracted at the outer surface of the object and reflected at the inner surface of the object at a fifth point of the object; and calculating a refractive index, n, of the object based on $v_s$, a, β, τ(0), τ($2R_D$), τ($x_{D2}$), τ($x_{d2}$) and τ($x_{d1}$), wherein calculating n includes calculating a difference between τ($2R_D$) and τ(0), and a difference between τ($x_{d2}$) and τ($x_{D2}$).

Aspects of the disclosure may include methods according to the following clauses 1 to 11.

1. A method for measuring a property of a transparent tubular object having a refractive index, n, and a longitudinal axis, the method including:

scanning a laser beam in a scanning direction with a constant scanning speed, $v_s$, along a scanning path at right angles to the longitudinal axis of the object, wherein the scanning laser beam is directed in a first laser beam direction to the object at right angles to the scanning direction and at right angles to the longitudinal axis of the object;

detecting an intensity of laser light originating from the object in a first detection direction parallel to the laser beam direction;

determining a first time, τ(0), and a second time, τ($2R_D$), from the intensity of the laser light detected in the first detection direction, τ(0) being representative of the laser beam being tangential to the outer surface of the object at a first point of the object, and τ($2R_D$) being representative of the laser beam being tangential to the outer surface of the object at a second point of the object diametrically opposite the first point;

detecting an intensity of laser light originating from the object in a second detection direction at a detection angle, a, greater than zero to the first detection direction;

determining a third time, τ($x_{D2}$), and a fourth time, τ($x_{d2}$), from the intensity of the laser light detected in the second detection direction, τ($x_{D2}$) being representative of the laser beam being reflected at the outer surface of the object at a third point of the object, and τ($x_{d2}$) being representative of the laser beam being refracted at the outer surface of the object and reflected at the inner surface of the object at a fourth point of the object; and calculating an inner radius, $R_d$, of the object based on n, $v_s$, a, τ(0), τ($2R_D$), τ($x_{D2}$) and τ($x_{d2}$), wherein calculating $R_d$ includes calculating a difference between $\tau(2R_D)$ and $\tau(0)$, and a difference between $\tau(x_{d2})$ and $\tau(x_{D2})$.

2. A method for measuring a property of a transparent tubular object having a refractive index, n, and a longitudinal axis, the method including:

scanning a laser beam in a scanning direction with a constant scanning speed, $v_s$, along a scanning path at right angles to the longitudinal axis of the object, wherein the laser beam is directed at right angles to the longitudinal axis of the object, wherein the scanning laser beam is directed in a first laser beam direction to the object at right angles to the scanning direction in a first part of the scanning path, and redirected via a reflector in a second laser beam direction to the object at a scanning angle, β, greater than zero to the first laser beam direction in a second part of the scanning path;

detecting an intensity of laser light originating from the object in a first detection direction parallel to the first laser beam direction;

determining a first time, $\tau(0)$, and a second time, $\tau(2R_D)$, from the intensity of the laser light detected in the first detection direction, $\tau(0)$ being representative of the laser beam being tangential to the outer surface of the object at a first point of the object, and $\tau(2R_D)$ being representative of the laser beam being tangential to the outer surface of the object at a second point of the object diametrically opposite the first point;

detecting an intensity of laser light originating from the object in a second detection direction at a detection angle, a, to the first detection direction;

determining a third time, $\tau(x_{D2})$, and a fourth time, $\tau(x_{d2})$, from the intensity of the laser light detected in the second detection direction, $\tau(x_{D2})$ being representative of the laser beam being reflected at the outer surface of the object at a third point of the object, and $\tau(x_{d2})$ being representative of the laser beam being refracted at the outer surface of the object and reflected at the inner surface of the object at a fourth point of the object; and calculating an inner radius, $R_d$, of the object based on n, $v_s$, a, β, $\tau(0)$, $\tau(2R_D)$, $\tau(x_{D2})$ and $\tau(x_{d2})$, wherein calculating $R_d$ includes calculating a difference between $\tau(2R_D)$ and $\tau(0)$, and a difference between $\tau(x_{d2})$ and $\tau(x_{D2})$.

3. A method for measuring a property of a transparent tubular object having a longitudinal axis, the method including:

scanning a laser beam in a scanning direction with a constant scanning speed, $v_s$, along a scanning path at right angles to the longitudinal axis of the object, wherein the scanning laser beam is directed in a first laser beam direction to the object at right angles to the scanning direction and at right angles to the longitudinal axis of the object;

detecting an intensity of laser light originating from the object in a first detection direction parallel to the first laser beam direction;

determining a first time, $\tau(0)$, and a second time, $\tau(2R_D)$, from the intensity of the laser light detected in the first detection direction, $\tau(0)$ being representative of the laser beam being tangential to the outer surface of the object at a first point of the object, and $\tau(2R_D)$ being representative of the laser beam being tangential to the outer surface of the object at a second point of the object diametrically opposite the first point;

detecting an intensity of laser light originating from the object in a second detection direction at a detection angle, a, greater than zero to the first detection direction;

determining a third time, $\tau(x_{D2})$, and a fourth time, $\tau(x_{d2})$, from the intensity of the laser light detected in the second detection direction, $\tau(x_{D2})$ being representative of the laser beam being reflected at the outer surface of the object at a third point of the object, and $\tau(x_{d2})$ being representative of the laser beam being refracted at the outer surface of the object and reflected at the inner surface of the object at a fourth point of the object;

determining a fifth time, $\tau(x_{d1})$, from the intensity of the laser light detected in the first detection direction, $\tau(x_{d1})$ being representative of the laser beam being refracted at the outer surface of the object and reflected at the inner surface of the object at a fifth point of the object; and calculating an inner radius, $R_d$, of the object based on $v_s$, a, $\tau(0)$, $\tau(2R_D)$, $\tau(x_{D2})$, $\tau(x_{d2})$ and $\tau(x_{d1})$, wherein calculating $R_d$ includes calculating a difference between $\tau(2R_D)$ and $\tau(0)$, and a difference between $\tau(x_{d2})$ and $\tau(x_{D2})$.

4. A method for measuring a property of a transparent tubular object having a longitudinal axis, the method including:

scanning a laser beam in a scanning direction with a constant scanning speed, $v_s$, along a scanning path at right angles to the longitudinal axis of the object, wherein the laser beam is directed at right angles to the longitudinal axis of the object, wherein the scanning laser beam is directed in a first laser beam direction to the object at right angles to the scanning direction in a first part of the scanning path, and redirected via a reflector in a second laser beam direction to the object at a scanning angle, β, greater than zero to the first laser beam direction in a second part of the scanning path;

detecting an intensity of laser light originating from the object in a first detection direction parallel to the laser beam direction;

determining a first time, $\tau(0)$, and a second time, $\tau(2R_D)$, from the intensity of the laser light detected in the first detection direction, $\tau(0)$ being representative of the laser beam being tangential to the outer surface of the object at a first point of the object, and $\tau(2R_D)$ being representative of the laser beam being tangential to the outer surface of the object at a second point of the object diametrically opposite the first point;

detecting an intensity of laser light originating from the object in a second detection direction at a detection angle, a, to the first detection direction;

determining a third time, $\tau(x_{D2})$, and a fourth time, $\tau(x_{d2})$, from the intensity of the laser light detected in the second detection direction, $\tau(x_{D2})$ being representative of the laser beam being reflected at the outer surface of the object at a third point of the object, and $\tau(x_{d2})$ being representative of the laser beam being refracted at the outer surface of the object and reflected at the inner surface of the object at a fourth point of the object;

determining a fifth time, $\tau(x_{d1})$, from the intensity of the laser light detected in the first detection direction, $\tau(x_{d1})$ being representative of the laser beam being refracted at the outer surface of the object and reflected at the inner surface of the object at a fifth point of the object; and calculating an inner radius, $R_d$, of the object based on $v_s$, a, β, $\tau(0)$, $\tau(2R_D)$, $\tau(x_{D2})$, $\tau(x_{d2})$ and $\tau(x_{d1})$, wherein calculating $R_d$ includes calculating a difference between $\tau(2R_D)$ and $\tau(0)$, and a difference between $\tau(x_{d2})$ and $\tau(x_{D2})$.

5. The method according to clause 1, wherein $R_d$ is calculated based on the equation:

$$R_d = R_D \cdot \frac{1 - \frac{x_{d2}}{R_D}}{n \cdot \sin\left(\frac{\alpha}{2} + \arcsin\left(\frac{1 - \frac{x_{d2}}{R_D}}{n}\right) - \arcsin\left(1 - \frac{x_{d2}}{R_D}\right)\right)},$$

wherein:

$$R_D = \frac{v_s}{2} \cdot (\tau(2R_D) - \tau(0))$$

and $$x_{d2} = R_D \cdot \left(\frac{2(\tau(x_{d2}) - \tau(x_{D2}))}{\tau(2R_D) - \tau(0)} + 1 - \sin(\alpha/2)\right).$$

6. The method according to clause 2, wherein $R_d$ is calculated based on the equation:

$$R_d = R_D \cdot \frac{1 - \frac{x_{d2}}{R_D}}{n \cdot \sin\left(\frac{\alpha+\beta}{2} + \arcsin\left(\frac{1 - \frac{x_{d2}}{R_D}}{n}\right) - \arcsin\left(1 - \frac{x_{d2}}{R_D}\right)\right)},$$

wherein:

$$R_D = \frac{v_s}{2} \cdot (\tau(2R_D) - \tau(0))$$

and $$x_{d2} = R_D \cdot \left(\frac{2(\tau(x_{d2}) - \tau(x_{D2}))}{\tau(2R_D) - \tau(0)} + 1 - \sin((\alpha+\beta)/2)\right).$$

7. The method according to clause 3, wherein $R_d$ is calculated based on the equation:

$$R_d = R_D \frac{1}{b + \sqrt{b^2 - 1}}$$

wherein:

$$R_D = \frac{v_s}{2} \cdot (\tau(2R_D) - \tau(0)),$$

$$b = \frac{g\sin\beta_1 - \cos\left(\frac{\alpha}{2} - \beta_2\right)}{g - 1},$$

$$g = \left(\tan\beta_1 \frac{\sin\left(\frac{\alpha}{2} - \beta_2\right)}{\sin\beta_2}\right)^2,$$

$$\beta_1 = \arcsin\left(1 - \frac{x_{d1}}{R_D}\right),$$

$$\beta_2 = \arcsin\left(1 - \frac{x_{d2}}{R_D}\right),$$

$$x_{d1} = v_s \cdot (\tau(x_{d1}) - \tau(0)) = 2 \cdot R_d \cdot \frac{(\tau(x_{d1}) - \tau(0))}{(\tau(2R_D) - \tau(0))},$$

and $$x_{d2} = R_D \cdot \left(\frac{2(\tau(x_{d2}) - \tau(x_{D2}))}{\tau(2R_D) - \tau(0)} + 1 - \sin(\alpha/2)\right).$$

8. The method according to clause 4, wherein $R_d$ is calculated based on the equation:

$$R_d = R_D \frac{1}{b + \sqrt{b^2 - 1}}$$

wherein:

$$R_D = \frac{v_s}{2} \cdot (\tau(2R_D) - \tau(0)),$$

$$b = \frac{g\sin\beta_1 - \cos\left(\frac{\alpha+\beta}{2} - \beta_2\right)}{g - 1},$$

$$g = \left(\tan\beta_1 \frac{\sin\left(\frac{\alpha+\beta}{2} - \beta_2\right)}{\sin\beta_2}\right)^2,$$

$$\beta_1 = \arcsin\left(1 - \frac{x_{d1}}{R_D}\right),$$

$$\beta_2 = \arcsin\left(1 - \frac{x_{d2}}{R_D}\right),$$

$$x_{d1} = v_s \cdot (\tau(x_{d1}) - \tau(0)) = 2 \cdot R_d \cdot \frac{(\tau(x_{d1}) - \tau(0))}{(\tau(2R_D) - \tau(0))},$$

and $$x_{d2} = R_D \cdot \left(\frac{2(\tau(x_{d2}) - \tau(x_{D2}))}{\tau(2R_D) - \tau(0)} + 1 - \sin((\alpha+\beta)/2)\right).$$

9. The method according to any one of clauses 1, 3, 5, 7, wherein a is between 45° and 135°, in particular 90°.

10. The method according to any one of clauses 2, 4, 6, 8, 9, wherein α+β is between 45° and 135°, in particular 90°.

11. The method according to any one of clauses 1 to 8, further including:

polarizing the scanning laser beam in a 45° polarizing direction;

polarizing the laser light originating from the object in the first detection direction in a (−45+δ)° polarizing direction, wherein |δ|>0; and/or polarizing the laser light originating from the object in the second detection direction in a (45+ε)° polarizing direction, wherein |δ|>0.

As explained in detail above, in a method and apparatus for measuring a property of a transparent tubular object, a laser beam scans the object, and laser light originating from the object is detected in a first detection direction parallel to the laser beam direction, or in the first and in a second detection direction at an angle thereto, in particular at 90°. The inner radius of the object may be calculated from the refractive index, scanning speed, outer diameter detected in the first detection direction, and, in the second detection direction, the time difference between laser light reflected from the outer surface of the object and laser light refracted into the object and reflected at the inner surface thereof. If the time of detecting laser light refracted into the object and reflected at the inner surface thereof in the first detection direction is known, the refractive index is not required.

As required, detailed includes of the present invention are disclosed herein. However, it is to be understood that the disclosed includes are merely exemplary of the invention, which can be embodied in various forms. Further, the terms and phrases used herein are not intended to be limiting, but rather, to provide an understandable description of the invention.

The terms "a"/"an", as used herein, are defined as one or more than one. The term plurality, as used herein, is defined as two or more than two. The term another, as used herein, is defined as at least a second or more. The terms including and/or having, as used herein, are defined as comprising (i.e., open language, not excluding other elements or steps). Any reference signs in the claims should not be construed as limiting the scope of the claims or the invention.

The mere fact that certain measures are recited in mutually different dependent claims does not indicate that a combination of these measures cannot be used to advantage.

The term coupled, as used herein, is defined as connected, although not necessarily directly, and not necessarily mechanically.

The processor system may include one or more processors to fulfil the functions of several items recited in the claims. For this purpose, a computer program or computer software is provided including computer instructions loadable in the one or more processors to cause the one or more processors to fulfil the functions.

A computer program may be stored and/or distributed on a suitable medium, such as an optical storage medium or a solid-state medium supplied together with or as part of other hardware, but also be distributed in other forms, such as via the Internet or other wired or wireless telecommunication systems.

It is to be understood that the disclosed includes are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Furthermore, the terms and phrases used herein are not intended to be limiting, but rather, to provide an understandable description of the invention.

It is noted that the foregoing examples have been provided merely for the purpose of explanation and are in no way to be construed as limiting of the present invention. While the present invention has been described with reference to exemplary includes, it is understood that the words which have been used herein are words of description and illustration, rather than words of limitation. Changes may be made, within the purview of the appended claims, as presently stated and as amended, without departing from the scope and spirit of the present invention in its embodiments. Although the present invention has been described herein with reference to particular structures, materials and includes, the present invention is not intended to be limited to the particulars disclosed herein; rather, the present invention extends to all functionally equivalent structures, methods and uses, such as are within the scope of the appended claims.

The present invention is not limited to the above described includes, and various variations and modifications may be possible without departing from the scope of the present invention.

What is claimed is:

1. An apparatus for measuring a property of a transparent tubular object having a refractive index, n, and a longitudinal axis, the apparatus comprising:
    a laser beam scanner that scans a laser beam in a scanning direction with a constant scanning speed, $v_s$, along a scanning path at right angles to the longitudinal axis of the object, wherein the scanning laser beam is directed in a first laser beam direction to the object at right angles to the scanning direction and at right angles to the longitudinal axis of the object;
    a detector assembly that detects an intensity of laser light originating from the object in a first detection direction parallel to the first laser beam direction, and that detects an intensity of laser light originating from the object in a second detection direction at a detection angle, a, greater than zero to the first detection direction;
    a processor; and
    one or more memories which store an executable set of instructions, which when executed by the processor, cause the processor to execute operations including:
        determining a first time, $\tau(0)$, and a second time, $\tau(2R_D)$, from the intensity of the laser light detected in the first detection direction by the detector assembly, $\tau(0)$ being representative of the laser beam being tangential to the outer surface of the object at a first point of the object, and $\tau(2R_D)$ being representative of the laser beam being tangential to the outer surface of the object at a second point of the object diametrically opposite the first point;
        determining a third time, $\tau(x_{D2})$, and a fourth time, $\tau(x_{d2})$, from the intensity of the laser light detected in the second detection direction by the detector assembly, $\tau(x_{D2})$ being representative of the laser beam being reflected at the outer surface of the object at a third point of the object, and $\tau(x_{d2})$ being representative of the laser beam being refracted at the outer surface of the object and reflected at the inner surface of the object at a fourth point of the object; and
        calculating an inner radius, $R_d$, of the object based on n, $v_s$, a, $\tau(0)$, $\tau(2R_D)$, $\tau(x_{D2})$, and $\tau(x_{d2})$, wherein calculating $R_d$ comprises calculating a difference between $\tau(2R_D)$ and $\tau(0)$, and a difference between $\tau(x_{d2})$ and $\tau(x_{D2})$.

2. The apparatus according to claim 1, wherein the processor calculates $R_d$ based on the equation:

$$R_d = R_D \cdot \frac{1 - \frac{x_{d2}}{R_D}}{n \cdot \sin\left(\frac{\alpha}{2} + \arcsin\left(\frac{1 - \frac{x_{d2}}{R_D}}{n}\right) - \arcsin\left(1 - \frac{x_{d2}}{R_D}\right)\right)},$$

wherein:

$$R_D = \frac{v_s}{2} \cdot (\tau(2R_D) - \tau(0))$$

and $$x_{d2} = R_D \cdot \left(\frac{2(\tau(x_{d2}) - \tau(x_{D2}))}{\tau(2R_D) - \tau(0)} + 1 - \sin(\alpha/2)\right).$$

3. The apparatus according to claim 1 wherein a is between 45° and 135°.

4. The apparatus according to claim 1, wherein the detector assembly comprises:
    a first detector that detects the intensity of laser light originating from the object in the first detection direction; and
    a second detector, different from the first detector, and that detects the intensity of laser light originating from the object in the second detection direction.

5. The apparatus according to claim 4, wherein the detector assembly further comprises a reflector arranged between the object and the second detector, the reflector configured to reflect laser light originating from the object in the second detection direction towards the second detector.

6. The apparatus according to claim 5, wherein the reflector is further configured to reflect laser light originating from the object in the second detection direction to be in the first detection direction, the apparatus further comprising:

a laser beam polarizer arranged between the laser beam scanner and the object, the polarizer configured to polarize the laser beam;

a half-lambda plate, arranged between the object and the reflector, the half-lambda plate configured to rotate the polarization direction of the laser light originating from the object; and a polarizing beam splitter arranged and configured to split the laser light from the object and the reflector in the first detection direction, to the first detector and the second detector based on the polarization state of the laser light.

7. The apparatus according to claim 5, wherein the reflector comprises one of a pentagon prism or a mirror.

8. The apparatus according to claim 1, wherein the detector assembly comprises:

a reflector that reflects laser light originating from the object in the second detection direction to be in the first detection direction; and a first detector that detects the intensity of laser light originating from the object in the first detection direction, and that detects the intensity of laser light originating from the object in the second detection direction and being reflected by the reflector to be in the first detection direction.

9. The apparatus according to claim 1, further comprising at least one of:

a first polarizer having a 45° polarizing direction, and being arranged in the path of the scanning laser beam;

a second polarizer having a $(-45+\delta)°$ polarizing direction, and being arranged in the path of the laser light originating from the object in the first detection direction, wherein $|\delta|>0$; or a third polarizer having a $(45+\varepsilon)°$ polarizing direction, and being arranged in the path of the laser light originating from the object in the second detection direction, wherein $|\varepsilon|>0$.

10. An apparatus for measuring a property of a transparent tubular object having a refractive index, n, and a longitudinal axis, the apparatus comprising:

a laser beam scanner that scans a laser beam in a scanning direction with a constant scanning speed, $v_s$, along a scanning path at right angles to the longitudinal axis of the object, wherein the scanning laser beam is directed at right angles to the longitudinal axis of the object, wherein the scanning laser beam is directed in a first laser beam direction to the object at right angles to the scanning direction in a first part of the scanning path, and redirected via a reflector in a second laser beam direction to the object at a scanning angle, β, greater than zero to the first laser beam direction in a second part of the scanning path;

a detector assembly that detects an intensity of laser light originating from the object in a first detection direction parallel to the first laser beam direction, and that detects an intensity of laser light originating from the object in a second detection direction at a detection angle, a, to the first detection direction;

a processor; and one or more memories which store an executable set of instructions, which when executed by the processor, cause the processor to execute operations including:

determining a first time, $\tau(0)$, and a second time, $\tau(2R_D)$, from the intensity of the laser light detected in the first detection direction, $\tau(0)$ being representative of the laser beam being tangential to the outer surface of the object at a first point of the object, and $\tau(2R_D)$ being representative of the laser beam being tangential to the outer surface of the object at a second point of the object diametrically opposite the first point;

determining a third time, $\tau(x_{D2})$, and a fourth time, $\tau(x_{d2})$, from the intensity of the laser light detected in the second detection direction, $\tau(x_{D2})$ being representative of the laser beam being reflected at the outer surface of the object at a third point of the object, and $\tau(x_{d2})$ being representative of the laser beam being refracted at the outer surface of the object and reflected at the inner surface of the object at a fourth point of the object; and calculating an inner radius, $R_d$, of the object based on n, $v_s$, a, β, $\tau(0)$, $\tau(2R_D)$, $\tau(x_{D2})$ and $\tau(x_{d2})$, wherein calculating $R_d$ comprises calculating a difference between $\tau(2R_D)$ and $\tau(0)$, and a difference between $\tau(x_{d2})$ and $\tau(x_{D2})$.

11. The apparatus according to claim 10, wherein the processor calculates $R_d$ based on the equation:

$$R_d = R_D \cdot \frac{1 - \frac{x_{d2}}{R_D}}{n \cdot \sin\left(\frac{\alpha+\beta}{2} + \arcsin\left(\frac{1 - \frac{x_{d2}}{R_D}}{n}\right) - \arcsin\left(1 - \frac{x_{d2}}{R_D}\right)\right)},$$

wherein:

$$R_D = \frac{v_s}{2} \cdot (\tau(2R_D) - \tau(0))$$

and $$x_{d2} = R_D \cdot \left(\frac{2(\tau(x_{d2}) - \tau(x_{D2}))}{\tau(2R_D) - \tau(0)} + 1 - \sin((\alpha+\beta)/2)\right).$$

12. The apparatus according to claim 10 wherein α+β is between 45° and 135°.

13. An apparatus for measuring a property of a transparent tubular object having a longitudinal axis, the apparatus comprising:

a laser beam scanner that scans a laser beam in a scanning direction with a constant scanning speed, $v_s$, along a scanning path at right angles to the longitudinal axis of the object, wherein the scanning laser beam is directed in a first laser beam direction to the object at right angles to the scanning direction and at right angles to the longitudinal axis of the object;

a detector assembly that detects an intensity of laser light originating from the object in a first detection direction parallel to the first laser beam direction, and that detects an intensity of laser light originating from the object in a second detection direction at a detection angle, a, greater than zero to the first detection direction;

a processor; and one or more memories which store an executable set of instructions, which when executed by the processor, cause the processor to execute operations including:

determining a first time, $\tau(0)$, and a second time, $\tau(2R_D)$, from the intensity of the laser light detected in the first detection direction, $\tau(0)$ being representative of the laser beam being tangential to the outer surface of the object at a first point of the object, and $\tau(2R_D)$ being representative of the laser beam being tangential to the outer surface of the object at a second point of the object diametrically opposite the first point;

determining a third time, $\tau(x_{D2})$, and a fourth time, $\tau(x_{d2})$, from the intensity of the laser light detected in the second detection direction, $\tau(x_{D2})$ being representative of the laser beam being reflected at the outer surface of the object at a third point of the object, and $\tau(x_{d2})$ being representative of the laser beam being refracted at the outer surface of the object and reflected at the inner surface of the object at a fourth point of the object;

determining a fifth time, $\tau(x_{d1})$, from the intensity of the laser light detected in the first detection direction, $\tau(x_{d1})$ being representative of the laser beam being refracted at the outer surface of the object and reflected at the inner surface of the object at a fifth point of the object; and calculating an inner radius, $R_d$, of the object based on $v_s$, $\alpha$, $\tau(0)$, $\tau(2R_D)$, $\tau(x_{D2})$, $\tau(x_{d2})$ and $\tau(x_{d1})$, wherein calculating $R_d$ comprises calculating a difference between $\tau(2R_D)$ and $\tau(0)$, and a difference between $\tau(x_{d2})$ and $\tau(x_{D2})$.

14. The apparatus according to claim 13, wherein the processor calculates $R_d$ based on the equation:

$$R_d = R_D \frac{1}{b + \sqrt{b^2 - 1}}$$

wherein:

$$R_D = \frac{v_s}{2} \cdot (\tau(2R_D) - \tau(0)),$$

$$b = \frac{g \sin\beta_1 - \cos\left(\frac{\alpha}{2} - \beta_2\right)}{g - 1},$$

$$g = \left(\tan\beta_1 \frac{\sin\left(\frac{\alpha}{2} - \beta_2\right)}{\sin\beta_2}\right)^2,$$

$$\beta_1 = \arcsin\left(1 - \frac{x_{d1}}{R_D}\right),$$

$$\beta_2 = \arcsin\left(1 - \frac{x_{d2}}{R_D}\right),$$

$$x_{d1} = v_s \cdot (\tau(x_{d1}) - \tau(0)) = 2 \cdot R_d \cdot \frac{(\tau(x_{d1}) - \tau(0))}{(\tau(2R_D) - \tau(0))},$$

and $$x_{d2} = R_D \cdot \left(\frac{2(\tau(x_{d2}) - \tau(x_{D2}))}{\tau(2R_D) - \tau(0)} + 1 - \sin(\alpha/2)\right).$$

15. An apparatus for measuring a property of a transparent tubular object having a longitudinal axis, the apparatus comprising:

a laser beam scanner that scans a laser beam in a scanning direction with a constant scanning speed, $v_s$, along a scanning path at right angles to the longitudinal axis of the object, wherein the laser beam is directed at right angles to the longitudinal axis of the object, wherein the scanning laser beam is directed in a first laser beam direction to the object at right angles to the scanning direction in a first part of the scanning path, and redirected via a reflector in a second laser beam direction to the object at a scanning angle, $\beta$, greater than zero to the first laser beam direction in a second part of the scanning path;

a detector assembly that detects an intensity of laser light originating from the object in a first detection direction parallel to the laser beam direction, and that detects an intensity of laser light originating from the object in a second detection direction at a detection angle, a, to the first detection direction;

a processor; and one or more memories which store an executable set of instructions, which when executed by the processor, cause the processor to execute operations including:

determining a first time, $\tau(0)$, and a second time, $\tau(2R_D)$, from the intensity of the laser light detected in the first detection direction, $\tau(0)$ being representative of the laser beam being tangential to the outer surface of the object at a first point of the object, and $\tau(2R_D)$ being representative of the laser beam being tangential to the outer surface of the object at a second point of the object diametrically opposite the first point;

determining a third time, $\tau(x_{D2})$, and a fourth time, $\tau(x_{d2})$, from the intensity of the laser light detected in the second detection direction, $\tau(x_{D2})$ being representative of the laser beam being reflected at the outer surface of the object at a third point of the object, and $\tau(x_{d2})$ being representative of the laser beam being refracted at the outer surface of the object and reflected at the inner surface of the object at a fourth point of the object;

determining a fifth time, $\tau(x_{d1})$, from the intensity of the laser light detected in the first detection direction, $\tau(x_{d1})$ being representative of the laser beam being refracted at the outer surface of the object and reflected at the inner surface of the object at a fifth point of the object; and calculating an inner radius, $R_d$, of the object based on $v_s$, $\alpha$, $\beta$, $\tau(0)$, $\tau(2R_D)$, $\tau(x_{D2})$, $\tau(x_{d2})$ and $\tau(x_{d1})$, wherein calculating $R_d$ comprises calculating a difference between $\tau(2R_D)$ and $\tau(0)$, and a difference between $\tau(x_{d2})$ and $\tau(x_{D2})$.

16. The apparatus according to claim 15, wherein the processor calculates $R_d$ based on the equation:

$$R_d = R_D \frac{1}{b + \sqrt{b^2 - 1}}$$

wherein:

$$R_D = \frac{v_s}{2} \cdot (\tau(2R_D) - \tau(0)),$$

$$b = \frac{g \sin\beta_1 - \cos\left(\frac{\alpha + \beta}{2} - \beta_2\right)}{g - 1},$$

$$g = \left(\tan\beta_1 \frac{\sin\left(\frac{\alpha + \beta}{2} - \beta_2\right)}{\sin\beta_2}\right)^2,$$

$$\beta_1 = \arcsin\left(1 - \frac{x_{d1}}{R_D}\right),$$

$$\beta_2 = \arcsin\left(1 - \frac{x_{d2}}{R_D}\right),$$

$$x_{d1} = v_s \cdot (\tau(x_{d1}) - \tau(0)) = 2 \cdot R_d \cdot \frac{(\tau(x_{d1}) - \tau(0))}{(\tau(2R_D) - \tau(0))},$$

and

-continued
$$x_{d2} = R_D \cdot \left( \frac{2(\tau(x_{d2}) - \tau(x_{D2}))}{\tau(2R_D) - \tau(0)} + 1 - \sin((\alpha + \beta)/2) \right).$$

* * * * *